US009655360B2

(12) United States Patent
Franklin et al.

(10) Patent No.: US 9,655,360 B2
(45) Date of Patent: May 23, 2017

(54) NEMATICIDAL COMPOSITIONS AND METHODS OF USING THEM

(75) Inventors: Lanny Franklin, Atlanta, GA (US); Gary Ostroff, Worcester, MA (US); Elizabeth Cloud, legal representative, Houston, TX (US); Lanna Franklin Rudeseal, legal representative, Atlanta, GA (US)

(73) Assignee: Eden Research PLC (GB)

( * ) Notice: Subject to any disclaimer, the term of this patent is extended or adjusted under 35 U.S.C. 154(b) by 1439 days.

(21) Appl. No.: 10/586,597

(22) PCT Filed: Jan. 24, 2005

(86) PCT No.: PCT/GB2005/000240
§ 371 (c)(1),
(2), (4) Date: Apr. 4, 2008

(87) PCT Pub. No.: WO2005/070213
PCT Pub. Date: Aug. 4, 2005

(65) Prior Publication Data
US 2008/0220038 A1    Sep. 11, 2008

Related U.S. Application Data

(60) Provisional application No. 60/538,627, filed on Jan. 23, 2004, provisional application No. 60/572,804, filed on May 20, 2004.

(51) Int. Cl.
| *A01P 5/00* | (2006.01) |
| *A01N 31/04* | (2006.01) |
| *A01N 31/00* | (2006.01) |
| *A01N 31/16* | (2006.01) |
| *A01N 25/28* | (2006.01) |
| *A01N 27/00* | (2006.01) |
| *A01N 49/00* | (2006.01) |
| *A01N 31/02* | (2006.01) |
| *A01N 31/08* | (2006.01) |
| *A01N 35/02* | (2006.01) |
| *A01N 35/04* | (2006.01) |
| *A01N 25/26* | (2006.01) |
| *A01N 35/06* | (2006.01) |

(52) U.S. Cl.
CPC ............ *A01N 35/04* (2013.01); *A01N 25/28* (2013.01); *A01N 27/00* (2013.01); *A01N 31/02* (2013.01); *A01N 31/04* (2013.01); *A01N 31/08* (2013.01); *A01N 31/16* (2013.01); *A01N 35/02* (2013.01); *A01N 35/06* (2013.01); *A01N 49/00* (2013.01)

(58) Field of Classification Search
CPC .... A01N 31/08; A01N 49/00; A01N 2300/00; A01N 25/28; A01N 31/16; A01N 35/06; A01N 25/26; A01N 65/00; A01N 31/02; A01N 35/02; A01N 65/22; A01N 37/02; A01N 65/28; A01N 25/02; A01N 31/04

USPC ................. 424/406, 405, 408, 417
See application file for complete search history.

(56) References Cited

U.S. PATENT DOCUMENTS

| 3,499,765 | A | 3/1970 | Lendvay |
| 3,767,421 | A | 10/1973 | Gulstad et al. |
| 3,956,485 | A | 5/1976 | Willett et al. |
| 4,001,480 | A | 1/1977 | Shank |
| 4,032,551 | A | 6/1977 | Willett et al. |
| 4,049,828 | A | 9/1977 | Cole et al. |
| 4,310,554 | A | 1/1982 | Olson et al. |
| 4,534,983 | A | 8/1985 | Koene et al. |
| 4,611,608 | A | 9/1986 | Vos et al. |
| 4,617,945 | A | 10/1986 | Vos et al. |
| 4,696,863 | A | 9/1987 | Matsushita et al. ....... 428/402.2 |
| 4,743,620 | A | 5/1988 | Hodgin et al. |
| 4,810,646 | A | 3/1989 | Jamas et al. |
| 4,826,693 | A | 5/1989 | Smith et al. |
| 4,944,693 | A | 7/1990 | Puerner et al. |
| 4,963,583 | A | 10/1990 | Kunz et al. |
| 4,985,261 | A | 1/1991 | Kang et al. |
| 4,992,540 | A | 2/1991 | Jamas et al. |
| 5,001,155 | A | 3/1991 | Kuc et al. |
| 5,013,566 | A | 5/1991 | Sampson |
| 5,028,703 | A | 7/1991 | Jamas |
| 5,032,401 | A | 7/1991 | Jamas |
| 5,068,453 | A | 11/1991 | Kuwahara et al. |
| 5,078,904 | A | 1/1992 | Behan et al. |

(Continued)

FOREIGN PATENT DOCUMENTS

| AP | P/2006/003724 | 1/2005 |
| AP | P/2008/004524 | 8/2006 |
| AU | 2002323473 | 8/2002 |
| AU | 2005207622 | 1/2005 |
| AU | 2005245190 | 5/2005 |

(Continued)

OTHER PUBLICATIONS

Calvet et al Evaluation of natural compounds against Root-knot nematodes European J. of Plant Pathology Jul. 2001 vol. 107,# 6 pp. 601-605 (Abstract—BIOSIS Accession # 2001;534017doc. # prev200100534017).*

(Continued)

*Primary Examiner* — Audrea Buckley
(74) *Attorney, Agent, or Firm* — Akerman LLP

(57) ABSTRACT

There is disclosed method of killing nematodes comprising the step of applying an effective amount of a nematicidal composition comprising a terpene component and compositions suitable for use in the method. The terpene component is preferably in association with water, either as a solution or a suspension. An excipient may also be included, which is suitably hollow glucan particles which encapsulate the terpene component.

24 Claims, 5 Drawing Sheets

(56) References Cited

U.S. PATENT DOCUMENTS

| | | | |
|---|---|---|---|
| 5,082,936 | A | 1/1992 | Jamas et al. |
| 5,091,200 | A | 2/1992 | Kang et al. |
| 5,288,632 | A | 2/1994 | Pannell |
| 5,401,727 | A | 3/1995 | Rorstad et al. |
| 5,547,677 | A | 8/1996 | Wright et al. |
| 5,549,901 | A | 8/1996 | Wright et al. |
| 5,607,677 | A | 3/1997 | Jamas et al. |
| 5,618,840 | A | 4/1997 | Wright et al. |
| 5,622,548 | A | 4/1997 | Zou et al. |
| 5,629,021 | A | 5/1997 | Wright et al. |
| 5,662,915 | A | 9/1997 | Okioga et al. |
| 5,662,957 | A | 9/1997 | Wright et al. |
| 5,673,468 | A | 10/1997 | Pumpe et al. |
| 5,700,679 | A | 12/1997 | Wright et al. |
| 5,730,989 | A | 3/1998 | Wright |
| 5,756,136 | A | 5/1998 | Black et al. |
| 5,798,252 | A | 8/1998 | Hobson et al. |
| 5,849,956 | A | 12/1998 | Koga et al. |
| 5,919,838 | A | 7/1999 | Mizobuchi |
| 5,922,121 | A | 7/1999 | Kwan |
| 5,939,050 | A | 8/1999 | Iyer et al. |
| 5,977,186 | A | 11/1999 | Franklin et al. |
| 5,981,625 | A | 11/1999 | Zou et al. |
| 6,130,253 | A | 10/2000 | Franklin et al. |
| 6,187,439 | B1 | 2/2001 | Elwakil |
| 6,232,528 | B1 | 5/2001 | Scorza et al. |
| 6,242,594 | B1 | 6/2001 | Kelly et al. |
| 6,246,594 | B1 | 6/2001 | Matsuda ............... 363/17 |
| 6,261,540 | B1 | 7/2001 | Nelson |
| 6,306,450 | B1 | 10/2001 | Bank et al. |
| 6,444,448 | B1 | 9/2002 | Wheatcroft et al. ....... 435/101 |
| 6,465,640 | B1 | 10/2002 | Hood |
| 6,506,803 | B1 | 1/2003 | Baker, Jr. et al. |
| 6,524,998 | B1 | 2/2003 | Kloepper et al. |
| 6,534,078 | B1 | 3/2003 | Strzemiemski et al. |
| 6,685,954 | B2 * | 2/2004 | Jeannin ............... 424/405 |
| 6,723,358 | B1 | 4/2004 | van Lengerich et al. |
| 6,746,684 | B2 | 6/2004 | Kitagaki et al. ........... 424/419 |
| 6,849,276 | B1 | 2/2005 | Dufau et al. |
| 7,018,641 | B1 | 3/2006 | Momol et al. |
| 2002/0028256 | A1 | 3/2002 | Bessette |
| 2003/0152629 | A1 | 8/2003 | Shefer et al. |
| 2003/0180349 | A1 | 9/2003 | Franklin |
| 2003/0185956 | A1 | 10/2003 | Gradley |
| 2003/0191046 | A1 | 10/2003 | Krzysztof |
| 2003/0194454 | A1 | 10/2003 | Bessette et al. |
| 2003/0216488 | A1 | 11/2003 | Uchiyama et al. |
| 2003/0228402 | A1 | 12/2003 | Franklin et al. |
| 2003/0231978 | A1 | 12/2003 | Franklin ............... 422/4 |
| 2004/0022990 | A1 | 2/2004 | Sitabkhan |
| 2004/0054166 | A1 | 3/2004 | Sauter et al. ........... 536/123.12 |
| 2004/0096821 | A1 | 5/2004 | Keenan et al. |
| 2004/0248764 | A1 | 12/2004 | Franklin ............... 514/1 |
| 2005/0126908 | A1 | 6/2005 | Keenan et al. |
| 2005/0281781 | A1 | 12/2005 | Ostroff |
| 2006/0120974 | A1 | 6/2006 | Mcneight et al. |
| 2006/0127489 | A1 | 6/2006 | Crothers et al. |
| 2006/0165614 | A1 | 7/2006 | Nelson et al. |
| 2010/0040656 | A1 | 2/2010 | Franklin ............... 424/405 |
| 2010/0136102 | A1 | 6/2010 | Franklin ............... 424/451 |
| 2010/0272818 | A1 | 10/2010 | Franklin ............... 424/493 |
| 2014/0170198 | A1 | 6/2014 | Franklin ............... 424/493 |

FOREIGN PATENT DOCUMENTS

| | | | |
|---|---|---|---|
| AU | 2006321415 | | 8/2006 |
| AU | 2006321416 | | 8/2006 |
| CA | 2141761 | A | 2/1996 |
| CA | 2 382 740 | A1 | 8/2000 |
| CA | 2567333 | | 5/2005 |
| CN | 200580024514.X | | 5/2005 |
| DE | 197 20 604 | A1 | 5/1997 |
| EP | 0085805 | | 8/1983 |
| EP | 0242135 | * | 10/1987 .................... 424/401 |
| EP | 0414282 | | 2/1991 |
| EP | 0414283 | | 2/1991 |
| EP | 0460945 | A2 * | 11/1991 .................... 424/401 |
| EP | 0460945 | | 12/1991 |
| EP | 0528466 | | 2/1993 |
| EP | 0 819 759 | A1 | 1/1998 |
| EP | 0844909 | | 6/1998 |
| EP | 0913407 | | 5/1999 |
| EP | 1085812 | | 3/2001 |
| EP | 1106070 | | 6/2001 |
| EP | 1159882 | A2 | 12/2001 |
| EP | 1161878 | | 12/2001 |
| EP | 1161883 | | 12/2001 |
| EP | 2002757456 | | 8/2002 |
| EP | 1240380 | | 9/2002 |
| EP | 1413202 | | 4/2004 |
| EP | 2005708211 | | 1/2005 |
| EP | 2005744354 | | 5/2005 |
| EP | 1538197 | A1 | 6/2005 |
| EP | 2006765189 | | 8/2006 |
| EP | 2006765192 | | 8/2006 |
| GB | 1285244 | | 8/1972 |
| GB | 1362007 | | 7/1974 |
| GB | 1457098 | | 12/1976 |
| GB | 1513777 | | 6/1978 |
| GB | 2162147 | | 1/1986 |
| GB | 2394416 | | 4/2004 |
| GB | 2395124 | | 5/2004 |
| GB | 2396107 | | 6/2004 |
| GB | 2406053 | | 3/2005 |
| IN | 7201/DELNP/2006 | | 5/2005 |
| IN | 5081/DELNP/2008 | | 8/2006 |
| JP | 55064736 | | 5/1980 |
| JP | 591 268 75 | | 6/1984 |
| JP | 62294079 | | 12/1987 |
| JP | 632 994 49 | | 11/1988 |
| JP | 02067208 | | 3/1990 |
| JP | 0219 1961 | | 7/1990 |
| JP | 03212497 | | 9/1991 |
| JP | 06-116111 | | 4/1994 |
| JP | 8-243378 | | 9/1996 |
| JP | 9-67205 | | 3/1997 |
| JP | 200044878 | | 2/2000 |
| JP | 2000 139 051 | | 5/2000 |
| JP | 02027903 | | 1/2002 |
| JP | 04024042 | | 1/2004 |
| JP | 2007517431 | | 5/2005 |
| JP | 2008542816 | | 8/2006 |
| JP | 2008542817 | | 8/2006 |
| MX | PA/a/2004/001906 | | 8/2002 |
| MX | PA/a/2006/013420 | | 5/2005 |
| MX | MX/a/2008/0006927 | | 8/2006 |
| NZ | 531492 | | 8/2002 |
| NZ | 551644 | | 5/2005 |
| PH | 12006502324 | | 5/2005 |
| WO | WO 90/10946 | | 9/1990 |
| WO | WO 91/10772 | | 7/1991 |
| WO | WO 91/17741 | | 11/1991 |
| WO | WO 94/09653 | | 5/1994 |
| WO | WO 96/36433 | | 11/1996 |
| WO | WO 96/38055 | | 12/1996 |
| WO | WO 98/56340 | | 12/1998 |
| WO | WO 99/30691 | | 6/1999 |
| WO | WO 00/21364 | | 4/2000 |
| WO | WO 00/24259 | | 5/2000 |
| WO | WO 00/49865 | | 8/2000 |
| WO | WO 00/51435 | | 9/2000 |
| WO | WO 00/53020 | | 9/2000 |
| WO | WO 01/11006 | | 2/2001 |
| WO | WO 01/13727 | A1 | 3/2001 |
| WO | WO 02/02213 | | 1/2002 |
| WO | WO 02/12348 | | 2/2002 |
| WO | WO 02/056879 | | 7/2002 |
| WO | WO 02/085314 | | 10/2002 |
| WO | WO-03/020024 | | 3/2003 |
| WO | WO 03/020024 | | 3/2003 |
| WO | WO03/020024 | A2 * | 3/2003 .................... 424/401 |
| WO | WO/03/028451 | | 4/2003 |
| WO | WO 03/069993 | | 8/2003 |
| WO | WO 03/070286 | | 8/2003 |

(56) References Cited

FOREIGN PATENT DOCUMENTS

| WO | WO/03/089561 | 10/2003 |
|---|---|---|
| WO | WO2004034791 | 4/2004 |
| WO | WO 2004/037004 | 5/2004 |
| WO | WO 2004/037232 | 5/2004 |
| WO | WO 2004/045588 | 6/2004 |
| WO | WO 2004/084947 | 10/2004 |
| WO | WO 2005/070213 | 8/2005 |
| WO | WO-2005/070213 | 8/2005 |
| WO | WO 2005/102045 | 11/2005 |
| WO | WO 2005/102508 | 11/2005 |
| WO | WO 2005/104842 | 11/2005 |
| WO | WO 2005/113128 | 12/2005 |
| WO | WO-2005/113128 | 12/2005 |
| WO | WO 2006/100308 | 9/2006 |
| WO | WO-2007/063267 | 6/2007 |
| WO | WO/2007/063267 | 6/2007 |
| WO | WO-2007/063268 | 6/2007 |
| WO | WO/2007/063268 | 6/2007 |
| ZA | 200402367 | 8/2002 |
| ZA | 200610427 | 5/2005 |

OTHER PUBLICATIONS

Oka et al Nematocidal Acitivity of Essenetial Oils—Against Root-Knot Nematode—Phytopathology (90, # 7, 710-15, 2000) ABSTGACT—CROPU Accession # 2000-86249.*
Database WPI/Derwent, AN 1981-56184D [25], XP-002297964 (Abstract).
Database WPI/Derwent, AN 1981-56187D [31], XP-002297963 (Abstract).
Database WPI/Derwent, AN 198156193D [31], XP-002297962 (Abstract).
Database WPI/Derwent, AN 1985-047717 [08] and JP 19830113680 Jun. 24, 1983 XP-002297961 (Abstract).
Database WPI/Derwent, AN 1986-052832 [08] and JP 19840126875 Jun. 20, 1984 XP-002297960 (Abstract).
Database WPI/Derwent, AN 1986-207139 [25] and JP 19840259347 Dec. 10, 1984 XP-002297959 (Abstract).
Database WPI/Derwent, AN 1990-214404 [28] and JP 19880299449 Nov. 29, 1988 XP-002297958 (Abstract).
Database WPI/Derwent, AN 1992-045981 [06] and JP 19900191961 Jul. 20, 1990, XP-002297957 (Abstract).
Database WPI/Derwent, AN 1999-114787 [10] and JP 19970148744 Jun. 6, 1997, XP-002297956 (Abstract).
Database WPI/Derwent, AN 2002-262398 [31] and JP 20000139051 May 11, 2000, XP-002297955 (Abstract).
Database WPI/Derwent, AN 93-216621 and JP 910335687 Nov. 25, 1991, XP-002056937 (Abstract).
Deeley et al., "Use of Dienes' Stain to Detect Plant Diseases Induced by MIOs," Phytopathology. 69: 1169-1171, 1979.
Eden-Green "Culture of Other Microorganisms From Yellows—Diseased Plants," pp. 201-239. In M. J. D. A. P. G. Markham (Ed.), "Plant and Insect Mycoplasma Techniques." Croom and Helm, London. 1982.
Gunderson et al., "Genomic Diversity and Differentiation Among Phytoplasma Strains in 16S rRNA Groups I (Aster Yellows and Related Phytoplasmas) and III (X-Disease and Related Phytoplasmas)," International J. of Syst. Bact. 46 (1): 64-75, 1996.
Kirkpatrick B.C. & C.D. Smart—Phytoplasmas: can phylogeny provide the means to understand pathogenicity? Adv. Bot. Res., 21, 187-212 (1995).
Kirkpatrick, BC. Strategies for Characterizing Plant Pathogenic MIO and Their Effects on Plants, In T. Kosuge and E. W. Nester (Eds. ), Plant-Microbe interactions: Molecular and Genetic Perspectives, vol. 3, Mcgraw-Hill, NY pp. 241-293, 1989.
Kunkel, "Heat Cure of Aster Yellows in Periwinkles," Am. J. Botany 28: 761-769, 1941.
Lee et al., Revised Classification Scheme of Phytoplasmas Based on RFLP Analyses of 16s RNA and Ribosomal Protein Gene Sequence [Review]. International Journal of Systematic Bacteriology. 48: 1153-1169, 1998.
Lee et al., Universal Amplification and Analysis of Pathogen 16s Rdna for Classification and Identification of Mycoplasmalike Organisms. Phytopathology. 83: 834-842, 1993.
Lee et al.,"Genetic Interrelatedness Among Clover Proliferation Mycoplasmalike Organisms (MIOs) and Other MIOs Investigated by Nucleic Acid Hybridization and Restriction Fragment Length Polymorphism Analyses," Appl. Environ. Micro. 57 (12): 3565-3569, 199[1].
Markham, "The 'Yellows' Plant Diseases: Plant Hosts and Their Interaction With the Pathogens," pp. 82-100 In M. J. Daniels and P. G. Markham (Eds.), 1982.
McCoy and Williams, "Chemical Treatment for Control of Plant Mycoplasma Diseases," pp. 152-173, In M. J. Daniels and D. S. Williams (Eds.), Plant Insect Mycoplasma Techniques. London, Croom Helm, 1982.
Nandi, Effect of some volatile aldehydes, ketones, esters and terpenoids on growth and development of fungi associated with wheat grains in the field and in storage, Journal of Plant Diseases and Protection, 84(2):114-128 (1977), XP-001062894.
Razin et al., 1998, Molecular Biology and Pathogenicity of Mycoplasmas, Micro. Mol. Bio. Rev. 62: 1094-1156, 1998.
Reuveni, "Activity of trifloxystrobin against powdery and downey mildew diseases of grapevines," Can. J. Plant Pathol. 23:52-59 2001 Abstract.
Schafft et al., "Sensitive Detection and Identification of Mycoplasma-Like Organisms in Plants by Polymerase Chain Reactions," Biochem Biophys. Res. Comm. 186: 1503-1509, 1992.
Siddique et al., "Histopathology and Within-Plant Distribution of the Phytoplasma Associated With Australian Papaya Dieback," Plant Dis. 82 (10): 1112-1120, 1998.
Sinclair et al., Sampling and Histological Procedures for Diagnosis of Ash Yellows. Plant Disease. 73: 432-435, 1989.
Abid, M., Sultan, V., Zaki, M. J., Maqbool, M. A. 1997. Nematicidal properties of *Stoechospermum marginatum*, a seaweed. Pakistan Journal of Phytopathology. 9(2):143-147. Abstract.
Aikawa, T., Togashi, K. 1999. An effect of pine volatiles on departure of Bursaphelenchus xylophilus (Nematoda: aphelenchoididae) from Monochamus alternatus (Coleoptera: Cerambycidae). pp. 127-131 in Sustainability of pine forests in relation to pine wilt and decline. Proceedings of International Symposium. Shokado Shoten, Kyoto. Abstract.
Akao N, Goto Y, Kondo K, Tsuda Y. Changing chemosusceptibility in the second-stage larvae of Toxocara canis by long-term incubation. J Helminthol. Jun. 1993;67(2):145-50. Abstract.
Asakawa, Y. 1999. Phytochemistry of bryophytes. Biologically active terpenoids and aromatic compounds from liverworts. Ed. Romeo, J. T. pp. 319-342 in Phytochemicals in human health protection, nutrition, and plant defense. Kluwer Academic/Plenum Publishers, New York. Abstract.
Bae et al. 1998. Anti-Helicobacter pylori activity of herbal medicines. Biol. Pharm. Bull., 21(9) 990-992.
Bard et al. 1988. Geraniol interferes with membrane functions in strains of Candida and *Saccharomyces*. Lipids 23(6):534-538.
Bauske EM; Rodriguezkabana R; Estaun V; Kloepper JW; Robertson DG; Weaver CF; King PS. 1995. Management of Meloidogyne-Incognita on Cotton by use of Botanical Aromatic-Compounds. Nematropica 24: 143-150. Abstract.
Bauske, E. M., Backman, P. A., Harper, K. M., Brannen, P. M., Rodriguez-Kabana, R., Kloepper, J. W. 1997. Effect of botanical aromatic compounds and seed-surface pH on growth and colonization of cotton plant growth-promoting rhizobacteria. Biocontrol Science and Technology. 7(3):415-421. Abstract.
Blagburn, B. L. 2002. Changing trends in ectoparasite control. Eds. Thoday, K. L., Foil, C. S., Bond, R. pp. 59-68. Abstract.
Borris, R. P., Schaeffer, J. M. Antiparasitic agents from plants. 1992. pp. 117-158 in Phytochemical resources for medicine and agriculture. Eds. Nigg, H.N.; Seigler, D. Plenum Press, New York. Abstract.
Chaumont and Leger. 1992. Campaign against allergenic moulds in dwellings. Inhibitor properties of essential oil of Geranium 'Bourbon', citronellol, geraniol and citral. Ann Pharm Fr 50(3):156-166. Abstract.

(56) References Cited

OTHER PUBLICATIONS

Chavarria-Carvajal, Jose A. 1997. Use of Organic Amendments and Naturally Occurring Aromatic Compounds for Control of Plant-Parasitic Nematodes: Effects on Microbial Activity and Soil Enzymes (Meloidogyne Incognita, Phytonematodes, Benzaldehyde, Biological Control). Auburn University. vol. 58-07b. Abstract.

Chitwood DJ. Phytochemical based strategies for nematode control. Annu Rev Phytopathol. 2002;40:221-49. Abstract.

Chitwood, D. J. 1993. Naturally occurring nematicides. Eds. Duke, S. O., Menn, J. J., Plimmer, J. R. pp. 300-315 in Pest control with enhanced environmental safety. American Chemical Society (ACS), Washington. Abstract.

Crowell and Gould. 1994. Chemoprevention and therapy of cancer by d-limonene. Crit Rev Oncog 5(1):1-22.

Crowell et al., 1996. Antitumorigenic effects of limonene and perillyl alcohol against pancreatic and breast cancer . . . Adv Exp Med Biol 401:131-136.

Duke, S. O. 1991. Plant terpenoids as pesticides. pp. 269-296 in Handbook of natural toxins. vol. 6. Toxicology of plant and fungal compounds. Eds. Keeler, R.F.; Tu, A.T. Marcel Dekker, Inc., New York. Abstract.

Elegbede et al., 1984. Inhibition of DMBA-induced mammary cancer by the monoterpene d-limonene. Carcinogenesis 5(5):661-664.

Elegbede et al., 1986. Regression of rat primary mammary tumors following dietary d-limonene. J Natl Cancer Inst 76(2):323-325.

Elson and Yu, 1994. The chemoprevention of cancer by mevalonate-derived constituents of fruits and vegetables. J Nutr. 124:607-614.

Enwerem, N. M., Okogun, J. I., Wambebe, C. O., Okorie, D. A., Akah, P. A.. 2001. Anthelmintic activity of the stem bark extracts of Berlinia grandiflora and one of its active principles, betulinic acid. Phytomedicine 8(2):112-114. Abstract.

Estaun, V., Camprubi, A., Calvet, C., Pinochet, J., Rodriguez-Kabana, R. 2001. Evaluation of natural chemical compounds against root-lesion and root-knot nematodes and side-effects on the infectivity of arbuscular mycorrhizal fungi. European Journal of Plant Pathology. 107(6); 601-605. Abstract.

Firman, K., Kinoshita, T., Itai, A., Sankawa, U. 1988. Terpenoids from Curcuma heyneana. Phytochemistry. 27(12):3887-3891. Abstract.

Hooser, et al., 1986. Effects of an insecticidal dip containing d-limonene in the cat. J Am Vet Med Assoc 189(8):905-908.

Ishii, 1993. Antibacterial activity of teprenone, a non water-soluble antiulcer agent, against helicobacter pylori. Int J Med Microbiol virol Parasitol Infect Dis 280(1-2):239-243.

JinNian, Z., Ping, J., CangSong, W., ShengLi, S., LiYuan, J., ChangChun, L.. 2000. Studies on Monochamus alternatus attractants and the attractability. Forest Research, Beijing 13(3):262-267. Abstract.

Kadota et al. 1997. Antibacterial activity of trichorabdal A from Rabdosia trichocarpa against Helicobacter pylori. Zentralblatt fur Bakteriologie. 286(1):63-7.

Karlson et al., 1996. Inhibition of tumor cell growth by monoterpenes in vitro: evidence of a Ras-independent mechanism of action. Anticancer Drugs 7(4):422-429.

Khoshkhoo, N., Hedin, P. A., McCarty, J. C., Jr. 1994. Terpenoid aldehydes in root-knot nematode susceptible and resistant cottonseeds as determined by HPLC and aniline methods. Journal of Agricultural and Food Chemistry. 42(3):804-806. Abstract.

Khoshkhoo, N., Hedin, P.A., McCarty, J.C. Terpenoid aldehydes in root-knot nematode susceptible and resistant cotton plants. J. Agric. Food Chem.; 1994; 42(1) pp. 204-208. Abstract.

Khoshkhoo, N., Hedin, P.A., McCarty, J.C.. Effects of bioregulators on the terpenoid aldehydes in root-knot nematode infected cotton plants. J. Agric. Food Chem.; 1993; 41(12) pp. 2442-2446. Abstract.

Kim et al., 1995. Antibacterial Activity of Some Essential Oil Components against Five Foodborne Pathogens. J Agric Food Chem 43:2839-2845.

Kokalis-Burelle, N., Kloepper, J. W., Rodriguez-Kabana, R. 1999. Organic amendments and natural chemicals as components of transplant mixes for control of root-knot nematode. Phytopathology. 89(6 Suppl.): S41. Abstract.

Mahajan, R., Singh, P., Bajaj, K. L., Kalsi, P. S. 1986. Nematicidal activity of some sesquiterpenoids against rootknot nematode (Meloidogyne incognita). Nematologica. 32(1):119-123. Abstract.

Mangel, M. S., Sangwan, N. K., Dhindsa, K. S., Verma, K. K., Bhatti, D. S. 1987. Nematicidal efficacy of some monoterpenes and related derivatives. Pesticides. 11(5):30-32. Abstract.

Mikhlin et al. 1983. Antifungal and antimicrobial activity of beta-ionone and vitamin A derivatives]. Prikl Biokhim Mikrobiol. 19:795-803 Abstract.

Milman, I. A. Alanto- and isoalantolactones. 1990. Chemistry of Natural Compounds. 26(3):251-262. Abstract.

Moleyar and Narasimham, 1992. Antibacterial activity of essential oil components. Int J Food Microbiol 16(4):337-342.

Momin, R. A., Ramsewak, R. S., Nair, M. G. 2000. Bioactive compounds and 1,3-diŸ(cis)-9-octadecenoyl-2-Ý(cis,cis)-9,12-octadecadienoylglycerol from Apium graveolens L. seeds. Journal of Agricultural and Food Chemistry. 48(9):3785-3788. Abstract.

Owawunmi. Letters in Applied Microbiology, 1993, 9(3): 105-108.

Pattnaik, et al. 1997. Antibacterial and antifungal activity of aromatic constituents of essential oils. Microbios 89(358):39-46.

Rodriguez-Kabana, R. 2002. Soil fumigation: New uses for old chemicals and new compounds. Nematology 4(2):156. Abstract.

Salt et al., 1986. Adam Physiol Molec Plant Path 28:287-297.

Sangwan, N. K., Verma, K. K., Verma, B. S., Mali, M. S., Dhindsa, K. S. 1985. 1985. Nematicidal activity of essential oils of Cymbopogon grasses. Nematologica. 31(1):93-99. Abstract.

Soler-Serratosa, A., Kokalis-Burelle, N., Rodriguez-Kabana, R., Weaver, C. F., King, P. S. 1996. Allelochemicals for control of plant-parasitic nematodes 1. In vivo nematicidal efficacy of thymol and thymol/benzaldehyde combinations. Nematropica. 26(1):57-71. Abstract.

Tominaga, Y., Yamamoto, M., Kuwahara, Y., and Sugawara, R. 1984. Behavioral responses. of the pine wood nematode to terpenes. Agric. Biol. Chem. 48:519-520.

Vasudevan, P., Kashyap, S., Sharma, S. 1997. Tagetes: a multipurpose plant. Bioresource Technology. 62(1/2):29-35. Abstract.

Veech JA • Histochemical localization and nematoxicity of terpenoid aldehydes in cotton • J.Nematol.;(1979);v. 11(3) p. 240-246.

Vera, R. 1993. Chemical composition of the essential oil of Ageratum conyzoides L. (Asteraceae) from Reunion. Flavour and Fragrance Journal. 8(5):257-260. Abstract.

Willett,. J. D. (1980). Control mechanisms in nematodes. In Nematodes as Biological Models,. vol. 1 (ed. B. M. Zuckerman), pp. 197-225. Abstract.

Wuyts N., Eisen A., De Waele D., Swennen R. and Sági L., 2002. Potential of plant secondary metabolites to increase resistance against plant-parasitic nematodes. 8th Ph.D. Symposium on Applied Biological Sciences. Universiteit Gent, Belgium, Oct. 9, 2002. Mededelingen. Faculteit Landbouwkundige en Toegepaste Biologische Wetenschappen 67 (4):101-104. Abstract.

Xu, G., Su, Z. 1994. Study on the terpenoids in Pinus thunbergii Parl. infected with Bursaphelenchus xylophilus. Chemistry and Industry of Forest Products. 14(3):49-54. Abstract.

Xu, Y. L., Wang, D., Li, X. J., Fu, J. 1989. Abietane quinones from Rabdosia lophanthoides. Phytochemistry. 28(1):189-191. Abstract.

Yu, SG, Anderson PJ, Elson, CE 1995. The efficacy of B-ionone in the chemoprevention of rat mammary carcinogenesis. J Agric Food Chem 43: 2144-2147.

Zhao, Z., Li, D., Hu, X., Xu, F., Sun, Z., Hu, G., Liu, X. 1999. Study on variations of neutral terpenoids of resistant provenances of P. massoniana after inoculating Bursaphelenchus xylophilus. pp. 217-221 in Sustainability of pine forests in relation to pine wilt and decline. Proceedings of International Symposium. Shokado Shoten, Kyoto. Abstract.

(56) References Cited

OTHER PUBLICATIONS

ZhenDong, Z., DongMei, L., XiE, H., FuYuan, X., Zhen, S., GuiXian, H., XianZhang, L. 2001. Study on chemical components and resistance mechanism to pine wood nematode of Masson pine provenance (II):—study on the components of neutral terpenoids and their differences among different resistant provenances of Pinus massoniana. Chemistry and Industry of Forest Products. 21(1): 56-60. Abstract.
ZhenDong, Z., XiE, H., DongMei, L., FuYuan, X., GuiXian, H., Zhen, S., XianZhang, L. 2001. Study on chemical components and resistance mechanism to pine wood nematode of masson pine provenance (III). Chemistry and Industry of Forest Products. 21(3):52-58. Abstract.
Zinovieva, S. V., Vasyukova, N. I., Ozeretskovskaya, I. L. 1990. Involvement of plant sterols in the system tomatoes—nematode *Meloidogyne incognita*. Helminthologia 27(3):211-216. Abstract.
International Preliminary Report on Patentability issued Jun. 3, 2008 for International Patent Application PCT/GB2006/002878 filed Aug. 3, 2006 and published as WO 2007/063267 on Jun. 7, 2007 (Inventor—Gary Ostroff // Applicant—Eden Research PLC) (7 pages).
Non-Final Rejection issued Apr. 9, 2014 for U.S. Appl. No. 12/095,580, filed Jul. 23, 2009 (Inventor—Lanny Franklin // Applicant—Eden Research PLC) (30 pages).
Final Rejection issued Oct. 2, 2013 for U.S. Appl. No. 12/095,580, filed Jul. 23, 2009 (Inventor—Lanny Franklin // Applicant—Eden Research PLC) (24 pages).
Response filed Sep. 6, 2013 for U.S. Appl. No. 12/095,580, filed Jul. 23, 2009 (Inventor—Lanny Franklin // Applicant—Eden Research PLC) (19 pages).
Non-Final Rejection issued Jun. 6, 2013 for U.S. Appl. No. 12/095,580, filed Jul. 23, 2009 (Inventor—Lanny Franklin // Applicant—Eden Research PLC) (24 pages).
Final Rejection issued Jul. 25, 2012 for U.S. Appl. No. 12/095,580, filed Jul. 23, 2009 (Inventor—Lanny Franklin // Applicant—Eden Research PLC) (20 pages).
Response filed Mar. 22, 2012 for U.S. Appl. No. 12/095,580, filed Jul. 23, 2009 (Inventor—Lanny Franklin // Applicant—Eden Research PLC) (16 pages).
Non-Final Rejection issued Dec. 22, 2011 for U.S. Appl. No. 12/095,580, filed Jul. 23, 2009 (Inventor—Lanny Franklin // Applicant—Eden Research PLC) (15 pages).
Response to Restriction Requirement filed Oct. 24, 2011 for U.S. Appl. No. 12/095,580, filed Jul. 23, 2009 (Inventor—Lanny Franklin // Applicant—Eden Research PLC) (12 pages).
Restriction Requirement issued Jun. 24, 2011 for U.S. Appl. No. 12/095,580, filed Jul. 23, 2009 (Inventor—Lanny Franklin // Applicant—Eden Research PLC) (15 pages).
Preliminary Amendment filed Feb. 25, 2014 for U.S. Appl. No. 14/188,790, filed Feb. 25, 2014 (Inventor—Lanny Franklin // Applicant—Eden Research PLC) (7 pages).
Final Rejection issued Nov. 5, 2013 for U.S. Appl. No. 12/095,584, filed Aug. 28, 2009 (Inventor—Lanny Franklin // Applicant—Eden Research PLC) (22 pages).
Final Rejection issued Apr. 17, 2012 for U.S. Appl. No. 12/095,584, filed Aug. 28, 2009 and published as 2010/0136102 on Jun. 3, 2010 (Inventor—Lanny Franklin // Applicant—Eden Research PLC) (19 pages).
Response filed Mar. 5, 2012 for U.S. Appl. No. 12/095,584, filed Aug. 28, 2009 (Inventor—Lanny Franklin // Applicant—Eden Research PLC) (21 pages).
Non-Final Rejection issued Oct. 7, 2011 for U.S. Appl. No. 12/095,584, filed Aug. 28, 2009 (Inventor—Lanny Franklin // Applicant—Eden Research PL) (15 pages).
Response filed Jun. 19, 2014 for U.S. Appl. No. 11/597,116, filed Jan. 24, 2005 (Inventor—Lanny Franklin // Applicant—Eden Research PLC) (16 pages).
Final Rejection issued Dec. 19, 2013 for U.S. Appl. No. 11/597,116, filed Jan. 24, 2005 (Inventor—Lanny Franklin // Applicant—Eden Research PLC) (24 pages).
Response filed Nov. 18, 2013 for U.S. Appl. No. 11/597,116, filed Jan. 24, 2005 (Inventor—Lanny Franklin // Applicant—Eden Research PLC) (19 pages).
Non-Final Rejection issued Jun. 18, 2013 for U.S. Appl. No. 11/597,116, filed Jan. 24, 2005 (Inventor—Lanny Franklin // Applicant—Eden Research PLC) (22 pages).
Response filed Oct. 12, 2012 for U.S. Appl. No. 11/597,116, filed Jan. 24, 2005 (Inventor—Lanny Franklin // Applicant—Eden Research PLC) (19 pages).
Non-Final Rejection issued Jul. 12, 2012 for U.S. Appl. No. 11/597,116, filed Jan. 24, 2005 (Inventor—Lanny Franklin // Applicant—Eden Research PLC) (18 pages).
Response filed Apr. 13, 2012 for U.S. Appl. No. 11/597,116, filed Jan. 24, 2005 (Inventor—Lanny Franklin // Applicant—Eden Research PLC) (18 pages).
Non-Final Rejection issued Dec. 13, 2011 for U.S. Appl. No. 11/597,116, filed Jan. 24, 2005 (Inventor—Lanny Franklin // Applicant—Eden Research PLC) (15 pages).
Response filed Jun. 27, 2011 for U.S. Appl. No. 11/597,116, filed Jan. 24, 2005 (Inventor—Lanny Franklin // Applicant—Eden Research PLC) (14 pages).
Requirement for Restriction issued Apr. 26, 2011 for U.S. Appl. No. 11/597,116, filed Jan. 24, 2005 (Inventor—Lanny Franklin // Applicant—Eden Research PLC) (8 pages).
Author Unknown (1998) "Yeast—better a friend than foe!" Food Processing, 67(9): 15-18.
Andes et al. (2000) Report of Successful prolonged antifungal therapy for refractory allergic fungal sinusitis. Clinical Infectious Diseases, 31(1): 202-204.
Bishop et al. 1998. Microencapsulation in yeast cells. J. Microencapsulation, 15(6): 761-773.
Calvet et al. (2001) Evaluation of natural compounds against Root-lesion and root-knot nematodes and side effects on the ineffectivity of arbuscular mycorrhizal fungi. European J. Plant Pathology. 107(6): 601-605.
Fleet CH, et al (1991). "Cell walls." The Yeasts, 4(2): 199-277.
Ladd TL, et al. (1974) Attraction of bumble bees and honey bees to traps baited with lures for the Japanese beetle. J Economic Entomology. 67(2): 307-308. (Abstract only).
Ladd TL. (1980) Japanese beetle: enhancement of lures by eugenol and caproic acid. J. Economic Entomology. 73(5): 718-720. (Abstract only).
Oka et al (2000) Nematodicidal activity of essential oils and their components against Root-knot nematode. Phytopathology. 90(7): 710-715.
Rattray et al. (1975). Lipids of yeasts. Bacteriological Reviews, 39(3): 197-231.
Sances et al. (1992) Minimization of pesticide residues on head lettuce: Within-head residue distribution of selected insecticides. J. Econ. Etymol. 85: 202.
Schmidt JO. (1994) Attraction of reproductive honey bee swarms to artificial nests by Nasonov pheromone. J Chemical Ecology. 20(5) 1053-1056.
Yokota M, et al. (1994) Antimicrobial effect of aromatic natural compound, chiefly against *Staphylococcus aureus*. Igaku to Seibutsugaku. 128(3): 105-110. (Abstract only).
Final Office Action issued Dec. 17, 2014 for U.S. Appl. No. 11/597,116, filed Oct. 27, 2008 (Inventor—Lanny Franklin // Applicant—Eden Research PLC) (18 pages).
Response to Office Action filed Jun. 17, 2015 for U.S. Appl. No. 11/597,116, filed Oct. 27, 2008 (Inventor—Lanny Franklin // Applicant—Eden Research PLC) (17 pages).
Final Office Action issued Sep. 11, 2015 for U.S. Appl. No. 11/597,116, filed Oct. 27, 2008 (Inventor—Lanny Franklin // Applicant—Eden Research PLC) (19 pages).
Response to Office Action filed Mar. 10, 2016 for U.S. Appl. No. 11/597,116, filed Oct. 27, 2008 (Inventor—Lanny Franklin // Applicant—Eden Research PLC) (18 pages).
Response to Office Action filed Sep. 17, 2012 for U.S. Appl. No. 12/095,584, filed Aug. 28, 2009 (Inventor—Lanny Franklin // Applicant—Eden Research PLC) (23 pages).

(56) References Cited

OTHER PUBLICATIONS

Response to Office Action filed May 4, 2014 for U.S. Appl. No. 12/095,584, filed Aug. 28, 2009 (Inventor—Lanny Franklin // Applicant—Eden Research PLC) (27 pages).
Final Office Action issued Jul. 8, 2014 for U.S. Appl. No. 12/095,584, filed Aug. 28, 2009 (Inventor—Lanny Franklin // Applicant—Eden Research PLC) (20 pages).
Response to Office Action filed Jan. 8, 2015 for U.S. Appl. No. 12/095,584, filed Aug. 28, 2009 (Inventor—Lanny Franklin // Applicant—Eden Research PLC) (22 pages).
Final Office Action issued Feb. 13, 2015 for U.S. Appl. No. 12/095,584, filed Aug. 28, 2009 (Inventor—Lanny Franklin // Applicant—Eden Research PLC) (19 pages).
Response to Office Action filed Aug. 13, 2015 for U.S. Appl. No. 12/095,584, filed Aug. 28, 2009 (Inventor—Lanny Franklin // Applicant—Eden Research PLC) (17 pages).
Supplemental Response to Office Action filed Sep. 4, 2015 for U.S. Appl. No. 12/095,584, filed Aug. 28, 2009 (Inventor—Lanny Franklin // Applicant—Eden Research PLC) (14 pages).
Non-Final Office Action issued Sep. 25, 2015 for U.S. Appl. No. 12/095,584, filed Aug. 28, 2009 (Inventor—Lanny Franklin // Applicant—Eden Research PLC) (23 pages).
Response to Office Action filed Mar. 25, 2016 for U.S. Appl. No. 12/095,584, filed Aug. 28, 2009 (Inventor—Lanny Franklin // Applicant—Eden Research PLC) (25 pages).
Final Office Action issued Apr. 26, 2016 for U.S. Appl. No. 12/095,584, filed Aug. 28, 2009 (Inventor—Lanny Franklin // Applicant—Eden Research PLC) (27 pages).
Non-Final Office Action issued Jul. 14, 2015 for U.S. Appl. No. 14/188,790, filed Feb. 25, 2014 (Inventor—Lanny Franklin // Applicant—Eden Research PLC) (15 pages).
Response to Office Action filed Jan. 13, 2016 for U.S. Appl. No. 14/188,790, filed Feb. 25, 2014 (Inventor—Lanny Franklin // Applicant—Eden Research PLC) (17 pages).
Final Office Action issued Mar. 16, 2016 for U.S. Appl. No. 14/188,790, filed Feb. 25, 2014 (Inventor—Lanny Franklin // Applicant—Eden Research PLC) (24 pages).
Rule 1.312 Amendment filed Jul. 6, 2016 for U.S. Appl. No. 12/095,580, filed Jul. 23, 2009 (Inventor—Lanny Franklin // Applicant—Eden Research PLC) (4 pages).
Rule 1.312 Amendment filed Jul. 6, 2016 for U.S. Appl. No. 12/095,580, filed Jul. 23, 2009 (Inventor—Lanny Franklin // Applicant—Eden Research PLC) (5 pages).
Response to Rule 1.312 Amendment issued Jun. 10, 2016 for U.S. Appl. No. 12/095,580, filed Jul. 23, 2009 (Inventor—Lanny Franklin // Applicant—Eden Research PLC) (2 pages).
Rule 1.312 Amendment filed Jun. 7, 2016 for U.S. Appl. No. 12/095,580, filed Jul. 23, 2009 (Inventor—Lanny Franklin // Applicant—Eden Research PLC) (4 pages).
Notice to File Corrected Application Papers issued May 27, 2016 for U.S. Appl. No. 12/095,580, filed Jul. 23, 2009 (Inventor—Lanny Franklin // Applicant—Eden Research PLC) (3 pages).
Notice of Allowance issued May 4, 2016 for U.S. Appl. No. 12/095,580, filed Jul. 23, 2009 (Inventor—Lanny Franklin // Applicant—Eden Research PLC) (11 pages).
Response to Non-Final Office Action filed Feb. 1, 2016 for U.S. Appl. No. 12/095,580, filed Jul. 23, 2009 (Inventor—Lanny Franklin // Applicant—Eden Research PLC) (24 pages).
Non-Final Office Action issued Jul. 30, 2015 for U.S. Appl. No. 12/095,580, filed Jul. 23, 2009 (Inventor—Lanny Franklin // Applicant—Eden Research PLC) (27 pages).
Response to Final Office Action filed Jul. 7, 2015 for U.S. Appl. No. 12/095,580, filed Jul. 23, 2009 (Inventor—Lanny Franklin // Applicant—Eden Research PLC) (26 pages).
Final Office Action issued Jan. 7, 2015 for U.S. Appl. No. 12/095,580, filed Jul. 23, 2009 (Inventor—Lanny Franklin // Applicant—Eden Research PLC) (25 pages).
Response to Non-Final Office Action filed Sep. 9, 2014 for U.S. Appl. No. 12/095,580, filed Jul. 23, 2009 (Inventor—Lanny Franklin // Applicant—Eden Research PLC) (15 pages).
Interview Summary issued on Jul. 22, 2014 for U.S. Appl. No. 12/095,580, filed Jul. 22, 2009 (Inventor—Lanny Franklin // Applicant—Eden Research PLC) (3 pages).
Interview Summary issued Mar. 7, 2017 for U.S. Appl. No. 12/095,584 filed Aug. 28, 2009 (Inventor—Lanny Franklin//Applicant—Eden Research PLC) (3 pages).
Non-Final Office Action issued Dec. 30, 2016 for U.S. Appl. No. 11/597,116 filed Oct. 27, 2008 (Inventor—Lanny Franklin//Applicant—Eden Research PLC) (25 pages).
Response to Office Action filed Feb. 3, 2017 for U.S. Appl. No. 14/188,790 filed Feb. 25, 2014 (Inventor—Lanny Franklin//Applicant—Eden Research PLC) (18 pages).

\* cited by examiner

NEMATICIDAL COMPOSITIONS AND METHODS OF USING THEM

CROSS REFERENCE TO RELATED APPLICATIONS

The present application claims priority to U.S. Provisional Patent Applications No. 60/538,627, filed Jan. 23, 2004, and No. 60/572,804, filed May 20, 2004, which applications are incorporated herein fully by this reference.

The present invention relates to nematicidal compositions comprising a terpene component, and to methods of killing nematodes by administration of a nematicidal composition comprising a terpene component.

Nematodes (Kingdom: Animalia, Phylum: Nematoda) are microscopic round worms. They can generally be described as aquatic, triploblastic, unsegmented, bilaterally symmetrical roundworms, that are colourless, transparent, usually bisexual, and worm-shaped (vermiform), although some can become swollen (pyroform). It is suggested that nematodes are the most abundant form of animal life and only about 3% of nematode species have been studied in detail.

Many nematodes are obligate parasites and a number of species constitute a significant problem in agriculture. It has been suggested that annual crop loss estimates caused by plant parasitic nematodes are roughly $80 billion worldwide, with $8 billion in the USA. Nematodes are a serious pest and methods to control their parasitic activities are an important feature in maximising crop production in modern intensive agriculture.

There are approximately 197 genera and 4300 species of nematode phytoparasites. Plant parasitic nematodes feed on the roots or shoots of plants. The nematodes can be ectoparasites (i.e. feed on the exterior of a plant) or endoparasites (i.e. live/feed inside the host) and can be migratory or sedentary.

Some of the most significant of the plant parastitic nematodes are:
Genus; Common name
*Meloidogyne*; Root-knot nematode
*Pratylenchus*; Lesion nematode
*Heterodera*; Cyst nematode
*Globodera*; Cyst nematode
*Ditylenchus*; Stem and bulb nematode
*Tylenchulus*; Citrus nematode
*Xiphinema*; Dagger nematode
*Radopholus*; Burrowing nematode
*Rotylenchulus*; Reniform nematode
*Helicotylenchus*; Spiral nematode
*Belonolaimus*; Sting nematode Nematodes are not just parasitic to plants but a number of species are parasitic to animals, both vertebrate and invertebrate. Around 50 species attack humans and these include Hookworm (*Anclyostoma*), Strongylids (*Strongylus*), Pinworm (*Enterolobius*), Trichinosis (*Trichina*), Elephantitis (*Wuchereria*), Heartworm (*Dirofilaria*), and Ascarids (*Ascaris*).

It should be noted however that not all nematodes inhabiting soil are phyto-parasitic. A number of saprophagous nematodes exist which do not harm plants, and indeed may actually exist in a symbiotic relationship with plants.

The current procedure for the elimination of nematodes in agriculture involves treating the soil with methyl bromide (MB). MB essentially sterilises the soil and provides effective control of a wide range of soil-borne pathogens and pests, including fungi, bacteria, nematodes, insects, mites, weeds and parasitic plants. However, MB has a significant negative impact on the environment.

Problems associated with MB include:
Eradication of the beneficial soil microflora and microfauna, resulting in elimination of natural biological control and resurgence of secondary pests and diseases. The "biological vacuum" created by the use of potent biocides, such as MB, results in rapid re-infestation of treated soils.
Toxic side-effects on humans, plants (phytotoxicity) and other non-target organisms. This has safety implications with regard to handling MB as any contact with the user would be harmful. There are therefore also major expenses involved with specialist equipment, training and other precautions involved with ensuring that MB is used, handled and transported safely.
MB is associated with the depletion of the ozone layer.
Pollution of the environment, including soil, water and the atmosphere. MB is, in particular, a major pollutant of underground water.
Pesticide residues in agricultural products, creating health risks for consumers and major obstacles to the international agricultural trade. Soil fumigation with MB is known to leave bromine residues in the soil which can be taken up by, and accumulate, in plants. Problems with bromine residues in leafy vegetables, such as lettuce, are quite common. Indeed, in grape producing regions the use of MB is not permitted due to its health implications.

For the reasons mentioned above, inter alia, the production and use of MB is being phased out on a global scale. Under the Montreal Protocol 1991, MB use is to be phased out by 2005 in the E.U. and other developed-countries, and by 2015 in the developing countries. There is therefore a need to identify suitable alternative solutions for managing soil-borne pathogens, in particular nematodes.

The inventor has surprisingly found that terpenes are effective in killing nematodes.

Terpenes are widespread in nature, mainly in plants as constituents of essential oils. Their building block is the hydrocarbon isoprene $(C_5H_8)_n$. Terpenes are classified as generally regarded as safe (GRAS) by the Environmental Protection Agency (EPA) in the USA and have been used in the flavour and fragrance industries.

Terpenes have been found to be effective and nontoxic dietary antitumor agents which act through a variety of mechanisms of action (Crowell and Gould, 1994—*Crit Rev Oncog* 5(1): 1-22; and Crowell et al., 1996—*Adv Exp Med Biol* 401: 131-136). Terpenes, i.e. geraniol, tocotrienol, perillyl alcohol, b-ionone and d-limonene, suppress hepatic HMG-COA reductase activity, a rate limiting step in cholesterol synthesis, and modestly lower cholesterol levels in animals (Elson and Yu, 1994—*J Nutr.* 124: 607-614). D-limonene and geraniol reduced mammary tumors (Elegbede et al., 1984—*Carcinogenesis* 5(5): 661-664; and Elegbede et al., 1986—*J Natl Cancer Inst* 76(2): 323-325; and Karlson et al., 1996—*Anticancer Drugs* 7(4): 422-429) and suppressed the growth of transplanted tumors (Yu et al., 1995—*J Agri Food Chem* 43: 2144-2147).

Terpenes have also been found to inhibit the in-vitro growth of bacteria and fungi (Chaumont and Leger, 1992—*Ann Pharm Fr* 50(3): 156-166; Moleyar and Narasimham, 1992—*Int J Food Microbiol* 16(4): 337-342; and Pattnaik, et al. 1997-*Microbios* 89(358): 39-46) and some internal and external parasites (Hooser, et al., 1986—*J Am Vet Med Assoc* 189(8): 905-908). Geraniol was found to inhibit growth of *Candida albicans* and *Saccharomyces cerevisiae* strains by enhancing the rate of potassium leakage and disrupting membrane fluidity (Bard et al., 1988-*Lipids* 23(6): 534-538).

B-ionone has antifungal activity which was determined by inhibition of spore germination, and growth inhibition in agar (Mikhlin et al., 1983—*Prikl Biokhim Mikrobiol.* 19: 795-803; and Salt et al., 1986—*Adam Physiol Molec Plant Path* 28: 287-297). Teprenone (geranylgeranylacetone) has an antibacterial effect on *H. pylori* (Ishii, 1993—*Int J Med Microbiol Virol Parasitol Infect Dis* 280(1-2): 239-243). Solutions of 11 different terpenes were effective in inhibiting the growth of pathogenic bacteria in in-vitro tests; levels ranging between 100 ppm and 1000 ppm were effective. The terpenes were diluted in water with 1% polysorbate 20 (Kim et al., 1995—*J Agric Food Chem* 43: 2839-2845). Diterpenes, i.e. trichorabdal A (from R. Trichocarpa) has shown a very strong antibacterial effect against *H. pylori* (Kadota et al., 1997—*Zentralblatt fur Bakteriologie.* 286(1):63-7). Rosanol, a commercial product with 1% rose oil, has been shown to inhibit the growth of several bacteria (*Pseudomona*, *Staphylococus*, *E. coli* and *H pylori*). Geraniol is the active component (75%) of rose oil.

In U.S. Pat. Nos. 5,977,186 and 6,130,253, methods of using terpenes to kill lice are disclosed.

In International Patent Application published under WO 03/020024, by the present inventor, methods of using terpenes to prevent and treat infections plants by bacteria, phytoplasmas, mycoplasmas or fungi are disclosed.

There may be different modes of action of terpenes against microorganisms; they could (1) interfere with the phospholipid bilayer of the cell membrane, (2) impair a variety of enzyme systems (HMG-reductase), and (3) destroy or inactivate genetic material. It is believed that due to the modes of action of terpenes being so basic, e.g., blocking of cholesterol, that infective agents will not be able to build a resistance to terpenes.

There are, however, a number of drawbacks to the use of terpenes. These include:

Terpenes are liquids which can make them difficult to handle and unsuitable for certain purposes.

Terpenes are not very miscible with water, and it generally requires the use of detergents, surfactants or other emulsifiers to prepare aqueous emulsions. A stable solution can, however, be obtained by mixing the terpenes under high shear.

Dry powder terpene formulations generally only contain a low percentage w/w of terpenes.

Terpenes are prone to oxidation in aqueous emulsion systems, which make long term storage a problem.

There are limitations to the current techniques of spray coating, extrusion, coacervation, molecular encapsulation, and spray drying/cooling to provide ingredient delivery systems.

Yeast cell walls are derived from yeast cells and are composed of the insoluble biopolymers $\beta$-1,3-glucan, $\beta$-1,6-glucan, mannan and chitin. They are typically 2-4 micron in diameter microspheres with a shell wall that is only 0.2-0.3 micron thick surrounding an open cavity. This material has considerable liquid holding capacity, typically absorbing 5-25 times its weight in liquid. The shell is sufficiently porous that payloads up to 150,000 Daltons in size can pass through the outer glucan shell and be absorbed into the hollow cavity of the spherical particle. Yeast cell walls have several unique properties, including heat stability (e.g. to 121° C.), shear stability, pH stability (e.g. pH 2-12), and at high concentrations they do not build significant viscosity. In addition to its physical properties this composition contains the natural and healthy dietary fibres that deliver cardiovascular and immunopotentiation health benefits.

Yeast cell walls are prepared from yeast cells by the extraction and purification of the insoluble particulate fraction from the soluble components of the yeast cell. The fungal cell walls can be produced from the insoluble byproduct of yeast extract manufacture. Further, the yeast cells can be treated with an aqueous hydroxide solution, without disrupting the yeast cell walls, which digests the protein and intracellular portion of the cell, leaving the yeast cell wall component devoid of significant protein contamination, and having substantially the unaltered cell wall structure of $\beta$(1-6) and $\beta$(1-3) linked glucans. A more detailed description of whole glucan particles and the process of preparing them is described by Jamas et al. in U.S. Pat. No. 4,810,646 and in co-pending patent applications U.S. Ser. Nos. 166, 929, 297,752 and 297,982. U.S. Pat. No. 6,242,594, assigned to Novogen Research Pty Ltd., describes a method of preparing yeast glucan particles by alkali extraction, acid extraction and then extraction with an organic solvent and finally drying. U.S. Pat. No. 5,401,727, assigned to AS Biotech-Mackzymal, discloses the methods of obtaining yeast glucan particles and methods of using them to promote resistance in aquatic animals and as an adjuvant for vaccinations. U.S. Pat. No. 5,607,677, assigned to Alpha-Beta Technology Inc., discloses the use of hollow whole glucan particles as a delivery package and adjuvant for the delivery of a variety of pharmaceutical agents. The teachings of the abovementioned patents and applications are incorporated herein by reference.

According to the present invention there is provided a method of killing nematodes, said method comprising the step of applying an effective amount of a nematicidal composition comprising a terpene component. Preferred features of the nematicidal composition are described below.

The terpene component may comprise a single terpene or a mixture of terpenes.

The list of terpenes which are exempted from US regulations found in EPA regulation 40 C. F. R. Part 152 is incorporated herein by reference in its entirety.

Preferably the terpene component comprises one or more terpenes selected from the group comprising citral, pinene, nerol, b-ionone, geraniol, carvacrol, eugenol, carvone, terpeniol, anethole, camphor, menthol, limonene, nerolidol, farnesol, phytol, carotene (vitamin A,), squalene, thymol, tocotrienol, perillyl alcohol, borneol, myrcene, simene, carene, terpenene and linalool.

It should also be noted that terpenes are also known by their extract or essential oil names, e.g. lemongrass oil (contains citral).

A suitable terpene component may comprise, for example:

100% citral;
50% citral and 50% b-ionone;
50% citral and 50% a-terpineol;
50% d-limonene and 50% b-ionone; or
50% a-terpineol and 50% b-ionone.

It has been found that compositions comprising citral are particularly effective at killing nematodes. Therefore it is preferred that the nematicidal composition of the present invention comprises citral.

It is highly preferable that all compounds present in the nematicidal composition are classified as generally regarded as safe (GRAS).

The term "terpene" as used herein refers not only to terpenes of formula $(C_5H_8)_n$, but also encompasses terpene derivatives, such as terpene aldehydes. In addition, reference to a single name of a compound will encompass the various isomers of that compound. For example, the term citral includes the cis-isomer citral-a (or geranial) and the trans-isomer citral-b (or neral).

In a preferred embodiment the nematicidal composition comprises a terpene component and water. The terpene component may be in solution in the water. Alternatively the nematicidal composition may comprise a surfactant which holds the terpene in suspension in the water. Suitable surfactants include, sodium lauryl sulphate, polysorbate 20, polysorbate 80, polysorbate 40, polysorbate 60, polyglyceryl ester, polyglyceryl monooleate, decaglyceryl monocaprylate, propylene glycol dicaprilate, triglycerol monostearate, TWEEN, Tween 80, SPAN 20, SPAN 40, SPAN 60, SPAN 80, Brig 30 or mixtures thereof. Sodium lauryl sulphate is a preferred surfactant due to its recognised safety.

In one embodiment of the invention the nematicidal composition has a pH of less than 7, suitably a pH from around 3 to less than 7, and preferably a pH from around 3 to around 5. Where the nematicidal composition has a pH below 7 the nematicidal activity of the composition does not decrease over time compared to a composition having a pH over 7.

Suitably the nematicidal composition comprises the terpene component at a concentration from about 125 to about 2000 ppm in water, preferably from about 250 to about 1000 ppm. A terpene component concentration from about 500 to about 2000 ppm may be preferred if higher kill rates are desired.

In one embodiment of the invention the terpene component is provided at a concentration at which parasitic nematodes are killed selectively over non-parasitic nematodes. Suitably the parasitic nematodes are root-knot nematodes and the non-parasitic nematodes are Saprophagous nematodes.

Suitable concentrations include from 250 to 1000 ppm, and preferably from 250 to 750 ppm.

The nematicidal composition may also comprise an excipient. The excipient may suitably comprise a liposome. Certain excipients may augment the action of the terpene component by, for example, increasing its longevity of action or by increasing its capacity to contact and interact with nematodes.

A particularly preferred excipient is hollow glucan particles. The term "hollow glucan particle" as used herein includes any hollow particle comprising glucan as a structural component. Thus, in particular, the term includes yeast cell walls (in purified or crude forms) or other hollow glucan particles, which may be hollow whole glucan particles.

It has been found that terpenes can be taken up and stably encapsulated within hollow glucan particles.

According to a further aspect of the present invention there is provided a method of killing nematodes, said method comprising the step of applying an effective amount of a nematicidal composition comprising a hollow glucan particle encapsulating a terpene component.

Nematicidal compositions comprising a hollow glucan particle encapsulating a terpene component can provide the following advantages:
maximise terpene payload;
minimise unencapsulated payload;
control payload stability;
control payload release kinetics;
creation of a solid form of a liquid terpene to increase the mass and uniformity;
simplify handling and application of terpenes; and
mask the smell and taste of the terpene.

Preferably the hollow glucan particles are yeast cell walls. Yeast cell walls are preparations of yeast cells that retain the three-dimensional structure of the yeast cell from which they are derived. Thus they have a hollow structure which allows the terpene component to be encapsulated within the yeast cell walls. The yeast walls may suitably be derived from Baker's yeast cells (available from Sigma Chemical Corp., St. Louis, Mo.).

Alternative particles are those known by the trade names SAF-Mannan (SAF Agri, Minneapolis, Minn.) and Nutrex (Sensient Technologies, Milwaukee, Wis.). These are hollow glucan particles that are the insoluble waste stream from the yeast extract manufacturing process. During the production of yeast extracts the soluble components of partially autolyzed yeast cells are removed and the insoluble residue is a suitable material for terpene loading. These hollow glucan particles are ~25-35% glucan w/w. A key attribute of these materials are that they are >10% lipid w/w and are very effective at absorbing terpenes. In addition, as a waste stream product they are a relatively cheap cost source of hollow glucan particles.

Alternative hollow glucan particles which have higher purity are those produced by Nutricepts (Nutricepts Inc., Burnsville, Minn.) and ASA Biotech. These particles have been alkali extracted, which removes additional intracellular components as well as removes the outer mannoprotein layer of the cell wall yielding a particle of 50-65% glucan w/w. Since alkali extraction saponifies some of the lipids these particles are less effective at absorbing terpenes. They are also significantly more expensive and hence these materials are preferred particles.

Higher purity hollow glucan particles are the WGP particles from Biopolymer Engineering. These particles are acid extracted removing additional yeast components yielding a product 75-85% glucan w/w. They are even more expensive than the Nutricepts and ASA Biotech particles and the lower lipid content results in poor loading with terpenes.

Very high purity hollow glucan particles are WGP from Alpha-beta Technology, Inc. (Worcester, Mass.) and microparticulate glucan from Novogen (Stamford, Conn.). These particles are organic solvent extracted removing residual lipids and are >90% glucan w/w.

Of all of the materials tested so far, these particles absorbed the least terpenes.

Situations may, however, be envisaged where a high purity glucan particle is required, for example, where tight control over possible contaminants is required. In these instances the higher purity particles would be preferred over the more crude products, despite their poorer terpene loading characteristics.

Preferably the hollow glucan particles have a slight lipid content. A slight lipid content can increase the ability of the hollow glucan particle to encapsulate the terpene component. Preferably the lipid content of the hollow glucan particles is greater than 5% w/w, more preferably greater than 10% w/w.

For encapsulation into a hollow glucan particle the terpene component of the present invention can optionally be associated with a surfactant. The surfactant can be nonionic, cationic, or anionic. Examples of suitable surfactants include sodium lauryl sulphate, polysorbate 20, polysorbate 80, polysorbate 40, polysorbate 60, polyglyceryl ester, polyglyceryl monooleate, decaglyceryl monocaprylate, propylene glycol dicaprilate, triglycerol monostearate, Tween®, Tweeri 80, Span® 20, Span® 40, Span® 60, Span® 80, Brig 30 or mixtures thereof. The surfactant acts to hold the terpene component in an emulsion and also assists encapsulation of the terpene component into the hollow glucan particle.

The nematicidal composition of the invention can comprise hollow glucan particles encapsulating a terpene component which comprise 1 to 99% by volume terpene component, 0 to 99% by volume surfactant and 1 to 99% hollow glucan particles. More specifically the hollow glucan particles encapsulating a terpene component can comprise from about 10% to about 67% w/w terpene component, about 0.1-10% surfactant and about 40-90% hollow glucan particles. A stable suspension of hollow glucan particles incorporating citral of 25 ppt citral can be made.

Suitably a nematicidal composition comprises from about 500 to about 10,000 ppm hollow glucan particles, where the particles contain from about 1 to about 67% terpene component. Preferably the nematicidal composition comprises from about 1000 to about 2000 ppm hollow glucan particles, where the particles contain from about 10 to about 50% terpene component.

The method is particularly suited to killing nematodes in soil, especially in soil used for agricultural or horticultural purposes. Such a method involves administering a nematicidal composition comprising a terpene component to at least a portion of, preferably all of, the soil to be treated.

Optionally the application of the nematicidal composition may be repeated. This may be necessary in some cases to ensure effective killing of the nematodes present in the portion of soil. The application of the nematicidal composition to soil may be carried out in a number of ways, including spraying, irrigation or the like.

In one embodiment the nematicidal composition used in the method of the present invention may be formed by mixing the terpene component and water with sufficient shear to create a solution of the terpene in water. Terpenes are generally poorly soluble in water, however, with mixing at sufficient shear they can be forced to form a stable solution in water. An aqueous terpene solution has the advantage that it can be taken up by plants through their roots, whereas an aqueous terpene suspension cannot.

In an alternative embodiment the nematicidal composition may be formed by adding a surfactant to hold the terpene component in aqueous suspension. Such a suspension would be useful where it is not necessary for the composition to be taken up by the plant, e.g. for treating an infection with ectoparasitic nematodes.

In an alternative embodiment the present invention further provides a method of preparing a nematicidal composition comprising hollow glucan particles encapsulating a terpene component, said method comprising the steps of;
 a) providing a terpene component;
 b) providing hollow glucan particles;
 c) incubating the terpene component with the glucan particles under suitable conditions for terpene encapsulation; and
 d) recovering the glucan particles encapsulating the terpene component.

Optionally the above method can further comprise the step of drying the glucan particles encapsulating the terpene component. Drying may be achieved in a number of ways and mention may be made of freeze drying, fluidised bed drying, drum drying or spray drying, all of which are well known processes.

In step a) of the above method, the terpene component is suitably provided as a suspension in an aqueous solvent, and optionally in the presence of a surfactant. Suitably the solvent is water. A suitable surfactant is Tween-80 (polyoxyethylenesorbitan monooleate) or sodium lauryl sulphate, and preferably the surfactant is present at a concentration of about 0.1 to 10% by volume of the total reaction mixture, more preferably about 1%. Alternatively the terpene component may be provided as a true solution in a solvent, e.g. water. A true solution of terpene in water can be obtained by mixing the terpene in water at high shear until a true solution is obtained. Publication No WO 03/020024 provides further details of forming true solutions of terpenes in water.

In step b) of the above method, the hollow glucan particles are suitably provided as a suspension in water or other suitable liquid. Suitably the suspension comprises approximately 1 to 1000 mg glucan particles per ml, preferably 200 to 400 mg/ml. Alternatively the hollow glucan particles may be provided as a dry powder and added to the terpene-surfactant suspension.

Alternatively the glucan particles are provided in sufficient liquid to minimally hydrate the particles, but not in significant excess. The term "hydrodynamic volume" (HV) is used to describe the volume of liquid required to minimally hydrate the particles. Thus suitably the particles are provided in between the HV and HV+50% of water. This makes the subsequent drying step more efficient. Also, where a low volume of water is used (ie. around HV to HV+50%), it is also possible to extrude the finished product into pellet or noodle form, which is convenient for fluidised bed drying.

It has been found that the terpene component can become encapsulated by the hollow glucan particles at room temperature. The rate of encapsulation is, however, increased at 37° C. but the temperature should be kept below the boiling point or denaturing temperature of any component of the composition. Suitable conditions for step c) of the above method are therefore atmospheric pressure at a temperature of 20 to 37° C. Optimisation of the conditions for a particular encapsulation reaction will be a matter of routine experimentation.

The present invention also provides the use of a nematicidal composition comprising a terpene component as described above for the extermination of nematodes, especially nematodes in soils and/or infecting plants.

It will be obvious to one skilled in the art that the nematicidal use of a composition made entirely of compounds which are GRAS is highly preferable over the use of prior art toxic compositions. Environmental concerns associated with use of the composition will be greatly reduced and there would be no significant problems with accumulation of the product in food crops. Additionally, regulatory approval of the composition in various jurisdictions would not be as difficult to obtain as for a toxic composition, and indeed may not even be required in some instances.

Embodiments of the present invention will now be described by way of example only, with reference to the figures in which.

EXAMPLE 1

Figure 1:
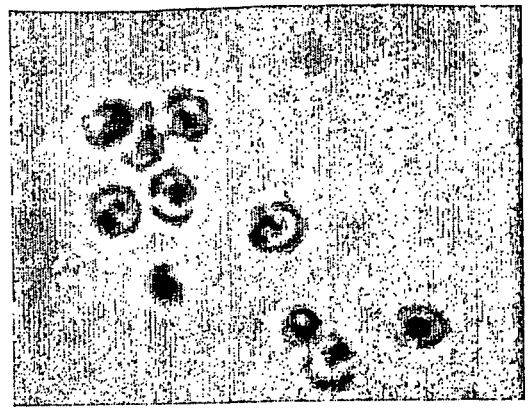
FIG. 1 represents a light micrograph of empty yeast cell walls.

Preparation of a Terpene Emulsion or Suspension Using a Surfactant

A terpene, terpene mixture, or liposome-terpene combination can be combined with a surfactant to form a suspension. The volumetric ratio of terpenes is generally about 1-99%, and the surfactant volumetric ratio is about 1-50% of the solution/mixture. The terpenes, comprised of natural or synthetic terpenes, are added to water. The surfactant, preferably polysorbate 80 or other suitable GRAS surfactant, is added to the water/terpene mixture and then blended to from a suspension. Citral is a suitable terpene.

EXAMPLE 2

Preparation of a Terpene Solution (without Surfactant)

The solution can be prepared without a surfactant by placing the terpene, e. g. citral, in water and mixing under solution-forming shear conditions until the terpene is in solution.

0.5 ml citral was added to 1 liter water. The citral and water were blended in a household blender for 30 seconds.

Alternatively, moderate agitation also prepared a solution of citral by shaking by hand for approximately 2-3 minutes.

Greater than about zero ppm to about 1000 ppm of natural or synthetic terpenes such as citral, b-ionone, geraniol, carvone, terpeniol, carvacrol, anethole, or other terpenes with similar properties are added to water and subjected to a solution-forming shear blending action that forces the terpene(s) into a true solution. The maximum level of terpene(s) that can be solubilized varies with each terpene. Examples of these levels are shown in Table 1.

TABLE 1

Solution levels for various terpenes.

| Terpene | Solution Level |
| --- | --- |
| Citral | 1000 ppm |
| Terpeniol | 500 ppm |
| b-ionone | 500 ppm |
| Geraniol | 500 ppm |
| Carvone | 500 ppm |

EXAMPLE 3

Potency of Solution

Terpenes will break down in the presence of oxygen. The rate at which they decay varies for each particular terpene.

Citral is a terpene aldehyde and will decay over a period of days. Two protocols are described below which quantify the rate of decay of citral.

The following protocol was used to determine the rate of decay of citral in a sealed container:

Test Material

A solution prepared as described in Example 2 containing citral at 1000 ppm was prepared in distilled water. This solution was stored in a capped glass vial for the duration of the test.

Procedure

A standard curve was prepared with citral and B-ionone as internal standard.

At the beginning of the study and weekly for four weeks the 1000 ppm suspension was analyzed using a gas chromatography procedure. The concentration of citral was determined by plotting it on the standard curve.

The results are shown below in Table 2.

TABLE 2

Stability of citral

| | Percentage of citral remaining | | | |
| --- | --- | --- | --- | --- |
| | Day 1 | Week 1 | Week 2 | Week 4 |
| Citral (1000 ppm) | 100 | 32 | 27 | 22 |

The following protocol was used to determine the rate of decay of citral in a container with a porous lid.

To determine the concentration of citral in water the following protocol was used.

Test Material

A solution containing citral at 1000 ppm was prepared in distilled water. This solution was stored in a beaker covered with porous paper for the duration of the test.

Procedure

A standard curve was prepared with citral and B-ionone as internal standard.

At the beginning of the study and after a week the 1000 ppm suspension was analyzed using a gas chromatography procedure. The concentration of citral was determined by plotting it on the standard curve.

The results are shown below in Table 3.

TABLE 3

Stability of citral

| | Percentage of citral remaining | |
|---|---|---|
| | Day 1 | Week 1 |
| Citral (1000 ppm) | 100 | 21.5% |

EXAMPLE 4

Extraction of Nematode Eggs from Soil and Counting Nematode Numbers

Extraction of Eggs and Quantification of Soil Populations

The following is an outline of a suitable technique to determine the population densities of soybean cyst nematodes SCN in soil samples, although it would be applicable to other soil nematodes. The procedure has three stages:
  extracting the cysts from the soil;
  crushing the cysts to extract the eggs; and,
  microscopic observation of the suspension of eggs for counting.

Extraction of Cysts from Soil

Cysts of soybean cyst nematode are recovered from soil through a combination of wet-sieving and decanting. The technique is a modification of the Cobb (Cobb, N. A. 1918. Estimating the nema population of soil. *U.S. Dept. Agr. Bur. Plant Ind. Agr. Tech. Cir.*, 1:1-48) sifting and gravity technique.

The procedure is as follows:
1. Combine a well mixed 100 cm$^3$ soil sample (approx. ½ cup) in a bucket with two (2) quarts (2.27 liters) of water.
2. Break any clumps with your fingers and mix the soil suspension well for 15 seconds.
3. Pour the soil suspension through an 8-inch-diameter #20 (850 mm pore) sieve into another bucket. Briefly rinse the debris caught on the 20 mesh sieve.
4. Pour the soil suspension in the second bucket through a #60 (250 mm pore) sieve.
5. Backwash the debris caught on the 60 mesh screen into a pan.
6. Repour the suspension through the 60 mesh screen—hold the screen at an angle to concentrate the cysts and debris.
7. Backwash into a pan using a minimal (<250 ml) amount of water.
8. Pour the cysts and debris into a 250 ml beaker. NOTE: Discard the heavier material that quickly settles to the bottom of the buckets/pans during the above sieving process.

Extraction of Eggs from the Cysts

The above technique will result in a suspension of SCN cysts, along with organic debris and sediments similar in size to the cysts. The cysts in this suspension could be counted using a simple dissecting microscope. Some laboratories that analyze soil for soybean cyst nematode report results in the form of cysts per 100 cm$^3$ of soil. Egg content of cysts is highly variable, and will not yield reliable counts of the SCN population in the sample. Therefore, it is preferable if eggs are extracted from the cysts and results are reported back as eggs and second stage juveniles (J-2) per 100 cm$^3$ of soil.

The procedure used to extract eggs from cysts is as follows:
1. Allow cysts/debris to settle for ca 30 minutes in the 250 ml beakers. Pour off excess water, resuspend sediments and transfer to 50 ml beakers.
2. Allow cysts to settle in the 50 ml beakers.
3. Pour off excess water (~30 ml) and transfer the cyst/debris suspension to a 55 ml Wheaton Potter-Elvehjen tissue grinder.
4. Grind at 7500 RPM for 10 seconds. Rinse pestle into grinding tube.
5. After grinding, pour the suspension in the tube through an 8-inch-diameter #200 (75 mm pore) sieve over a stainless steel #500 (25 mm pore) sieve.
6. Rinse the tube several times with tap water, each time pouring the contents through the sieves. Discard sediments caught on the #200 sieve.
7. Carefully wash sediments and eggs caught on the #500 sieve into a clean beaker with as little water as possible.

Counting Eggs with the Nematode Counting Slide:

The volume of the egg suspension should be brought up to exactly 50 ml with tap water. Fill the chamber of the nematode counting slide with a well-mixed suspension using a pipette. The specially made nematode counting slides are constructed so that the volume of egg suspension observed over the grid is exactly 1 ml. Consequently, simply count the number of eggs that appear within the grid of the slide to determine the number of eggs per ml of suspension. The total number of eggs in the sample can then be calculated by multiplying the number of eggs per ml by 50.

Sources of Materials and Equipment

Sieves:

Fisher Scientific, 1600 W. Glenlake Avenue, Itasca, Ill. 60143-(800) 223-9114

VWR Scientific, P.O. Box 66929, O'Hare AMF, Chicago, Ill. 60666-(800) 932-5000

Tissue Grinder:

Fisher Scientific, 1600 W. Glenlake Avenue, Itasca, Ill. 60143-(800) 223-9114

Motorized Stirrer:

The motorized laboratory stirrer is a Talboys Model 101 stirrer. This stirrer can be purchased through VWR Scientific or directly through Talboys Engineering Corporation, South Montrose, Pa. 18843.

Nematode Counting Slides:

The specially made nematode counting slides can be purchased from Advanced Equine Products, 5004 228th Avenue S.E., Issaquah, Wash. 98029, (425) 391-1169, FAX (425) 391-6669.

EXAMPLE 5

Effect of Terpenes on Nematode Egg Hatching and Juvenile Survival

The effect of various terpene containing compositions was assessed in relation to nematode eggs and juvenile nematodes.

The protocol used was as follows:

The live eggs were treated in the various samples for one hour, rinsed, put back into distilled water and counted 24 hours later. The samples were made up as shown in Table 4a:

TABLE 4a

| Sample | Components | | |
|---|---|---|---|
| NM1 | 10% Tween 80 | 45% d-limonene | 45% b-Ionone |
| NM3 | 10% Tween 80 | 45% citral | 45% b-Ionone |
| NM5 | 10% Tween 80 | 45% citral | 45% a-terpineol |
| NM6 | 10% Brig 30 | 45% a-terpineol | 45% b-Ionone |
| NM7 | 10% Tween 80 | 45% a-terpineol | 45% b-Ionone |

The results of the protocol are shown below in Table 4b.

TABLE 4b

Results

| Sample Designation | Conc. (%) | Egg batch (%) | Juveniles alive (%) |
|---|---|---|---|
| Control | — | 19 | 86 |
| NM1 | 0.5 | 3 | 0 |
|  | 0.1 | 10 | 19 |
|  | 0.05 | 17 | 67 |
| NM3 | 0.5 | 2 | 1 |
|  | 0.1 | 5 | 3 |
|  | 0.05 | 10 | 31 |
| NM5 | 0.5 | 4 | 0 |
|  | 0.1 | 9 | 16 |
|  | 0.05 | 16 | 37 |
| NM6 | 0.5 | 11 | 13 |
|  | 0.1 | 17 | 36 |
|  | 0.05 | 16 | 48 |
| N6 | 0.5 | 26 | 53 |
|  | 0.1 | 26 | 58 |
|  | 0.05 | 15 | 60 |
| NM7 | 0.5 | 13 | 74 |
|  | 0.1 | 13 | 58 |
|  | 0.05 | 17 | 75 |

Observations: The combinations containing citral (NM3 and NM5) were more effective. The Brig surfactant was not as effective as Tween 80. The aldehyde worked better than the alcohols.

EXAMPLE 6

Effect of Terpenes on Mature Root-Knot, Ring and Citrus Nematodes

The effect of various terpene containing compositions was assessed in relation to Root-Knot nematodes (*Meloidogyne*), Ring nematodes (*Criconemella xenoplax*) and Citrus nematodes (*Tylenchulus semipenetrans*).

The protocol used was as follows:

Nematodes: A single 5 ml volume with pre-counted nematode numbers was used as the initial inoculum. Nematodes were collected, identified and maintained from commercial agricultural crops soils. The nematodes were counted and evaluated for good health for the duration of the study.

Nematicidal compositions: In this protocol the terpene used in the nematicidal composition was citral. The relevant details of the citral used are as follows:
Chemical Name: CITRAL
Common Name: Lemongrass Oil
Formulation: CITRAL FCC
Product Trade Name: CITRAL FCC
Product code: 03-29200
Source: Penta Manufacturing
Lot Numbers: 77887
Type: Liquid
Carrier: Distilled Water
Storage Conditions: Ambient indoor room temperature ~65° F. (28.3° C.).
Stability: Insoluble in water above 1,000 ppm.

3 different concentrations of citral were used to assess the efficacy of terpenes in killing the nematodes. These were untreated control (UTC), 500 ppm and maximum soluble terpene concentration (900 ppm). The terpenes were combined with water as a solution by mixing at a solution forming shear. The 900 ppm concentration value was not be measured, but estimated at the maximum soluble concentration that can be obtained with distilled water at 65° F. (28.3° C.). 3 replicates of the 900 ppm concentration were used (R1, R2 and R3) and one replicate of the 500 ppm concentration and UTC.

Test mixtures of nematodes and the nematicidal compositions were made up according to Table 5.

TABLE 5

Test Mixtures

| Label | Nematode Vol. ml | Terpene Conc. ppm | Added Terpene Vol. Ml | Nematode + Terpene Vol. | Treatment Conc. ppm |
|---|---|---|---|---|---|
| UTC | 5.0 | 0.0 | 5.0 | 10.0 | 0.0 |
| 1.0 | 5.0 | 500.0 | 15.0 | 20.0 | 375.0 |
| R1 | 5.0 | 900.0 | 15.0 | 20.0 | 675.0 |
| R2 | 5.0 | 900.0 | 15.0 | 20.0 | 675.0 |
| R3 | 5.0 | 900.0 | 15.0 | 20.0 | 675.0 |

The terpene and nematode containing water was combined to form a final dilution volume and maintained in vials between evaluations. The nematodes were exposed to the terpenes for between 48 to 72 hours depending on their survival.

Evaluations: Nematodes were be counted and their appearance assessed by microscope. The microscope used for assay provided for only 5 ml to be viewed at one time. Therefore, the 20 ml of total terpene nematode sample water was divided into 4 parts for each assay and recombined afterwards. The rating of degree of efficacy of the test samples was determined by observing nematode mobility, mortality, and internal disruption or vacuolation over time.

The results are shown below in Table 6.

TABLE 6

Results

| | | | Root-Knot Meloidogyne | | Ring CX | | Citrus TS | |
|---|---|---|---|---|---|---|---|---|
| Day | Treatment | Time | Alive | Dead | alive | Dead | alive | dead |
| (pretreatment reading) | | | | | | | | |
| 1 | UTC | 11:00 am | 351 | 0 | 357 | 0 | 148 | 0 |
| 1 | 1.0 | 11:00 am | 359 | 0 | 325 | 0 | 119 | 0 |
| 1 | 20 ml-R1 | 11:00 am | 326 | 0 | 264 | 0 | 132 | 0 |
| 1 | 20 ml-R2 | 11:00 am | 347 | 0 | 260 | 0 | 141 | 0 |
| 1 | 20 ml-R3 | 11:00 am | 328 | 0 | 442 | 0 | 137 | 0 |
| (postreatment readings) | | | | | | | | |
| 1 | UTC | 6:00 pm | 348 | 0 | 350 | 0 | 144 | 0 |
| 1 | 1.0 | 6:00 pm | 355 | 0 | 319 | 0 | 114 | 0 |
| 1 | 20 ml-R1 | 6:00 pm | 320 | 0 | 258 | 0 | 128 | 0 |
| 1 | 20 ml-R2 | 6:00 pm | 341 | 0 | 255 | 0 | 139 | 0 |
| 1 | 20 ml-R3 | 6:00 pm | 325 | 0 | 436 | 0 | 134 | 0 |
| 2 | UTC | 6:00 am | 344 | 0 | 348 | 0 | 140 | 0 |
| 2 | 1.0 | 6:00 am | 350 | 0 | 312 | 0 | 112 | 0 |
| 2 | 20 ml-R1 | 6:00 am | 140 | 176 | 91 | 0 | 160 | 0 |
| 2 | 20 ml-R2 | 6:00 am | 168 | 169 | 110 | 141 | 46 | 84 |

TABLE 6-continued

Results

| Sample I.D. | | | Root-Knot Meloidogyne | | Ring CX | | Citrus TS | |
|---|---|---|---|---|---|---|---|---|
| Day | Treatment | Time | Alive | Dead | alive | Dead | alive | dead |
| 2 | 20 ml-R3 | 6:00 am | 137 | 184 | 181 | 248 | 70 | 59 |
| 2 | UTC | 6:00 am | 340 | 0 | 342 | 0 | 135 | 0 |
| 2 | 1.0 | 6:00 am | 340 | 6 | 304 | 4 | 101 | 8 |
| 2 | 20 ml-R1 | 6:00 am | 0 | 302 | 0 | 239 | 0 | 109 |
| 2 | 20 ml-R2 | 6:00 am | 0 | 322 | 0 | 236 | 0 | 116 |
| 2 | 20 ml-R3 | 6:00 am | 0 | 305 | 0 | 402 | 0 | 117 |
| 3 | UTC | 6:00 am | 330 | 3 | 336 | 1 | 126 | 5 |
| 3 | 1.0 | 6:00 am | 189 | 149 | 190 | 108 | 47 | 51 |

There was a small nematode loss from one reading to another due to nematodes hanging up on the sides of dishes and vials. These populations are usually under 5 nematodes per reading.

Observations:

Day 1—pretreatment readings showed no dead nematodes and the nematodes were all moving and had no internal disruption or vacuolation.

Day 1—6 pm (20 ml—R1+R2+R3) treatments all appeared to have slowed movement but they had no internal disruption or vacuolation.

Day 1—6 pm (1.0 and UTC) treatments showed no slowing of movement or internal disruption or vacuolation.

Day 2—6 am (UTC and 1.0) treatments all appeared normal with no loss of movement and no internal disruption or vacuolation.

Day 2—6 am (20 ml—R1+R2+R3) treatments had some dead (dead had no movement and their internal body structures were highly vacuolated). The living nematodes were still moving, although slowly, but no internal disruption or vacuolation.

Day 2—6 pm (UTC) treatment all appeared normal with no loss of movement and not internal disruption or vacuolation.

Day 2—6 pm (1.0) treatment had some dead. Dead had no movement with internal disruption and vacuolation. Some of the living had slowed movement and some did not, but none had any internal disruption or vacuolation.

Day 2—6 pm (20 ml—R1+R2+R3) treatments were all dead with no movement and internal disruption with vacuolation.

Day 3—6 am (UTC) treatments showed a few dead or dyeing nematodes. They had no movement but showed no internal disruption or vacuolation. The rest of the nematodes, listed as alive, still had good movement.

Day 3—6 am (1.0) treatments showed about 50% dead and both internal disruption and vacuolation. The alive nematodes showed some slowing of movement but no internal disruption or vacuolation.

As can be clearly seen from the results, on day two by 6 pm, compositions R1, R2 and R3 had killed all nematodes. This demonstrates the highly nematicidal properties of compositions R1, R2 and R3 and consequently the nematicidal properties of citral.

EXAMPLE 7

Effect of Citral Alone and Citral and Thymol on Root-Knot Nematode Juveniles

Treatment samples were prepared as follows:

Cital—1 ml citral was added to 400 ml of sterile distilled water and mixed using a household blender for 40 seconds. This was labelled 2500 ppm and was diluted to provide test solutions at 500, 250, 125 and 62.5 ppm.

Citral and Thymol—1.0 g of thymol was dissolved in 1 ml of citral and blended in 400 ml of water as for citral alone. This was marked 2500 ppm and diluted to provide test solutions at 500, 250, 125 and 62.5 ppm.

Control—Water was used as the control.

Nematode juveniles were collected in water and 0.1 to 0.15 ml added to each well of a plastic assay plate. 1.0 ml of the test solutions was added to each well. Observations were made microscopically after 24 and 48 hours as described in Example 4. Dead nematodes adopt a straight position and do not move when probed with a fine needle. Living nematodes move in an undulating, wave-like motion.

The results of two experiments are provided below in Tables 7 and 8. The figures given are for the percentage of nematodes found to be dead upon microscopic examination and are the average of 2 replicates.

TABLE 7

Effect of test solutions of root-knot juveniles after 24 and 48 hours

| | Citral and Thymol | | | Cital (ppm) | | | Control |
|---|---|---|---|---|---|---|---|
| Test (ppm) | 500 | 250 | 125 | 500 | 250 | 125 | Water |
| 24 h | 100 | 100 | 100 | 98 | 100 | 100 | 10 |
| 48 h | 100 | 91 | 50 | 97 | 91 | 24 | 31 |

TABLE 8

Effect of test solutions of root-knot juveniles after 24 hours.

| | Citral and Thymol | | | Cital (ppm) | | | Control |
|---|---|---|---|---|---|---|---|
| | | | Test (ppm) | | | | |
| | 250 | 125 | 62.5 | 250 | 125 | 62.5 | Water |
| 24 h | 97 | 96 | 94 | 94 | 94 | 98 | 6 |

The results demonstrate the ability of citral alone and a citral and thymol mixture to kill nematodes at low concentrations. Kill rates in table 7 after 48 hours were over 90% for both mixtures at 250 ppm and 500 ppm concentrations. The 125 ppm concentration showed a lower kill rate. The kill rates in Table 8 show high kill rates after 24 hours for concentration as low as 62.5 ppm.

The mixture of thymol and citral did not show a significant increase in kill rate over citral alone.

The results show that citral is an effective nematicide even at low concentrations.

EXAMPLE 8

Effects of Citral on Root-Knot Nematodes Vs Sarprophagous Nematodes

The purpose of this experiment was to demonstrate that citral selectively kills the harmful root-knot nematodes over saprophagus nematodes, which are not harmful, and indeed may be beneficial to the plant and soil. Such selective killing is a surprising effect that means treatment with terpenes may kill parasitic nematodes, but not eliminate the beneficial micro-fauna in the soil.

Aqueous text mixtures comprising 250 ppm citral alone and 250 ppm citral and 10% tween were produced according to the techniques described in Example 7 above. These compositions were then incubated with root-knot and saprophagus nematodes and the kill rate assessed microscopically. Living saprophagus nematodes move rapidly in water. The control used was the nematodes in water alone.

The results are provided in Tables 9 and 10 below. The figures given are for the percentage of nematodes found to be dead upon microscopic examination and are the average of 2 replicates.

TABLE 9

Nematicidal activity of citral on root-knot nematodes (% dead)

| | Citral + Tween 80 (250 ppm) | Citral (250 ppm) | Citral + Tween 80 (250 ppm) | Citral (250 ppm) | Control |
|---|---|---|---|---|---|
| 24 h | 87 | 87 | 89 | 88 | 17 |
| 48 h | 100 | 100 | 100 | 100 | 22 |

TABLE 10

Nematicidal activity of citral on Saprophagous nematodes (% dead)

| | Citral + Tween 80 (250 ppm) | Citral (250 ppm) | Citral + Tween 80 (250 ppm) | Citral (250 ppm) | Control |
|---|---|---|---|---|---|
| 24 h | 45 | 43 | 51 | 50 | 15 |
| 48 h | 50 | 50 | 53 | 52 | 19 |

The results clearly show that citral kills the pathogenic root-knot nematodes at a much higher kill rate than the beneficial saprophagus nematodes. After 48 hrs the kill rate for root-knot nematodes was 100% for all test mixtures, whereas for Saprophagus nematodes it was only 50-53%. The results were not significantly effected by the inclusion of Tween 80.

The results demonstrate that terpenes have the ability to selectively kill pathogenic nematodes whilst allowing beneficial nematodes to survive in the soil. This would result in a more healthy soil environment post treatment than a treatment which kills the entire nematode population in the soil. Firstly this is because beneficial nematodes would be present in the soil post treatment, and secondly there would not be a nematode "vacuum" in the soil which could be filled with pathogenic nematodes or other pathogens.

It could be expected that at a very high concentration of terpene may result in a higher kill rate of saprophagus nematodes, thus reducing the selectivity of the treatment. Therefore in use in the field the minimum concentration that achieves the desired kill rate in root-knot or other parasitic nematodes may be selected, thus maximising the selectivity.

EXAMPLE 9

Effect of pH on the Nematicidal Activity of Citral Containing Compositions

The following protocol was performed to assess the affect of pH on test solutions containing citral.

Solutions were made up of citral at 250, 125 and 62.5 ppm concentrations. Test solutions of these three concentrations were prepared at different pHs by adjusting the pH with HCl or NaOH to pH 4, 7 and 10.

One batch of test solutions was used immediately and another was left for 24 hours before use. The method of administration to the nematodes and counting the kill rate is the same as for previous protocols.

The results are shown below in Tables 11 and 12. The figures given are for the percentage of nematodes found to be dead upon microscopic examination and are the average of 2 replicates.

TABLE 11

Effect of fresh citral at three pH levels on root-knot nematodes (% nematodes dead)

| | 250 ppm | | | 125 ppm | | | 62.5 ppm | | | |
|---|---|---|---|---|---|---|---|---|---|---|
| | | | | PH | | | | | | |
| | 4 | 7 | 10 | 4 | 7 | 10 | 4 | 7 | 10 | Water |
| 24 h | 75 | 73 | 83 | 31 | 44 | 39 | 48 | 39 | 32 | 21 |
| 48 h | 73 | 72 | 87 | 50 | 47 | 39 | 50 | 44 | 45 | 30 |

TABLE 12

Effect of one-day old citral at three pH levels on root-knot nematodes (% nematodes dead)

| | 250 ppm | | | 125 ppm | | | 62.5 ppm | | | |
|---|---|---|---|---|---|---|---|---|---|---|
| | | | | PH | | | | | | |
| | 4 | 7 | 10 | 4 | 7 | 10 | 4 | 7 | 10 | water |
| 24 h | 90 | 40 | 47 | 27 | 25 | 25 | 40 | 30 | 16 | 10 |
| 48 h | 90 | 33 | 52 | 31 | 33 | 32 | 27 | 27 | 21 | 14 |

The results demonstrate that, in general, the test solutions lose efficacy if left for one day before use. However, it was observed that the citral solutions at the low pH (i.e. 4) did not lose efficacy to such an extent and, in fact the 250 ppm sample actually increased in efficacy after being left for a day. At all concentrations tested, the low pH samples did not demonstrate nearly such a significant a drop of efficacy after being left when compared to the neutral and high pH counterparts.

This demonstrates that low pH of citral is beneficial in terms of retaining the efficacy of citral as a nematocide over time. The reasons for this are unclear, but may be the result of stabilising the citral and preventing degradation.

It is therefore clear that adjusting the pH of a citral containing nematicidal composition to be acid (i.e. a pH below 7) would be beneficial in terms of prolonging its action.

EXAMPLE 10

Comparison of Nematicidal Activity High Purity Citral (98% Pure) with Low Purity Citral (80% Pure)

Citral is commercially available in 2 forms—regular (98% pure) and technical (80% pure). The following protocol was carried out to determine if technical citral is a viable-alternative to pure citral.

Compositions of regular and technical ciral at 250 and 125 ppm were produced in 1% Tween 80 and incubated with root-knot nematodes a in the same way as previously described. Observations of the kill rate (percentage dead) were made at 21 and 42 hours.

The results are shown below in Table 13 and are the average of four replicates.

TABLE 13

| | average percentage dead | | | | |
|---|---|---|---|---|---|
| | Citral (98% pure) | | Citral (80% pure) Ppm | | 1% Tween 80 | Water |
| | 250 | 125 | 250 | 125 | — | — |
| 21 h | 87 | 23 | 89 | 29 | 14 | 7 |
| 42 h | 87 | 22 | 96 | 27 | 17 | 18 |

The results indicate that both regular and technical citral kill nematodes effectively at concentrations of 250 ppm. Thus technical citral may be used as a cheaper alternative to regular citral.

EXAMPLE 11

Nematicidal Effects of Citral in Soil

The following protocol was carried out to assess the nematicidal properties of nematodes in soil.

Methodology: Nematodes used for the analysis originated from commercial agricultural crop soils. Species of nematode included root-knot and citrus. Prior to commencement of each study the nematodes were counted and evaluated for viability. In each experiment soil samples were infected with only one species of nematode. Three measured quantities of soil (250 g) were placed into large PVC plastic containers.

Soil moisture was assessed by weighing a soil sample and then drying the sample in a drying oven. Soil moisture content was confirmed using a "Hydroscout" instrument. In all cases the moisture content measured by both methods was within the resolution of the instruments. By determining the water content of the soil it was possible to calculate the volume of terpene solution which would be diluted when mixed with the soil.

A series of citral dilutions in water were prepared (500 ppm to 62.5 ppm) such that when they were added to the soil samples, they would yield the required ratios. These dilutions were by volume not the more commonly used mass ratios. The reason for using volume dilutions was simply one of convenience enabling the use of a micropipette or cylinder to measure the terpene. The mass ratio of the 'in soil' and 'in water' solution could be simply calculated by multiplying the ppm of terpene by it's density (0.92 g/ml).

The terpene solution was added to each test tube containing a weighed sample of nematode infected soil. The terpene solution and soil were mixed by inverting the test tube several times. The test tubes containing the soil and terpene solution were left to stand in racks in the laboratory for 48 hours-72 hours depending on the survival of the untreated nematodes. In each experiment a control group was treated with distilled water. The % mortality (kill) rates in the treatment groups was compared with the control population.

The nematodes were extracted by "Sieving & mist extraction" (Ayoub, S. M. 1977) prior to being counted.

Criteria for Evaluation: Nematode counts were performed to determine the proportion of nematodes which survived and were killed in each treatment group.

TABLE 14

| Pretreatment nematode counts | | |
|---|---|---|
| Sample ID | Root-Knot | Citrus |
| Mean nematode counts (N = 8) | 659.25 | 12,711.75 |

The results are shown below in Tables 15 and 16.

TABLE 15

| Treatment of Root Knot nematodes with terpene solution. | | |
|---|---|---|
| Terpene concentration | No of Replicates | Mean % killed |
| 500 ppm | 8 | 67.10 |
| 250 ppm | 8 | 23.66 |
| 125 ppm | 8 | 4.34 |
| 62.5 ppm | 8 | 18.87 |
| untreated | 8 | 5.71 |

TABLE 16

| Treatment of Citrus nematodes with terpene solution | | |
|---|---|---|
| Terpene concentration | No of Replicates | Mean % killed |
| 500 ppm | 8 | 95.53 |
| 250 ppm | 8 | 91.66 |
| 125 ppm | 8 | 46.29 |
| 62.5 ppm | 8 | -2.84 |
| untreated | 8 | 13.7 |

The protocol was repeated, this time using only citral at 500 ppm concentration. The results are shown below on Table 17 to 19.

TABLE 17

| Pretreatment nematode counts | | |
|---|---|---|
| Sample ID | Root-Knot | Citrus |
| Mean nematode counts (N = 8) | 1225.25 | 10755.5 |

TABLE 18

| Treatment of Root-Knot nematodes with terpene solution | | |
|---|---|---|
| Terpene concentration | N | Mean % killed |
| 500 ppm | 10 | 99.6 |

TABLE 19

| Treatment of Citrus nematodes with terpene solution | | |
|---|---|---|
| Terpene concentration | N | Mean % killed |
| 500 ppm | 10 | 99.9 |

The experiment was performed once again, this time with the following changes:
Dose range of 125 ppm-750 ppm was used.
Glass tubes containing 150 g of soil were used as opposed to PVC tubes in previous experiments.
The results are shown below in Table 20.

TABLE 20

Treatment of Root Knot nematodes with terpene solution

| Terpene concentration | N | Mean % killed |
|---|---|---|
| 750 ppm | 8 | 99.42 |
| 500 ppm | 8 | 100 |
| 250 ppm | 8 | 97.37 |
| 125 ppm | 8 | 74.51 |

The results all show that terpenes are effective nematicides in soil. This supports the data already provided showing that terpenes are effective nematicides in vitro. Concentrations of terpene as low as 125 ppm demonstate strong nematicidal activity in soil, though concentrations of 250 ppm and above showed more consistent high kill rates.

EXAMPLE 12

Demonstration of Terpene Loading into Bakers Yeast Particles and Purified Yeast Glucan Particles The following protocol was performed to demonstrate that terpenes would load into yeast cell walls and other yeast glucan particles.

Emulsions of citral and L-carvone were prepared by mixing 150 μl of the terpene with 100 μl of 10% Tween 80 in water and 250 μl of water.

Baker's yeast particles (YP) or Levacan™ yeast glucan particles (YGP), available from Savory Systems International, Inc., Branchburg, N.J., were mixed with water to form a 250 mg/ml suspension.

500 μl of the YP or YGP suspension and 250 μl of the terpene emulsion were mixed together and incubated overnight under constant agitation. 500 μl YP or YGP suspension and 500 μl of water were used as a control. The particles were then washed with water until free from external emulsion. The particle preparations were then frozen and lyophilised until dry.

The particles were then rehydrated and examined under light microscope. The results are shown in FIGS. 1 to 4.

Figure 2:
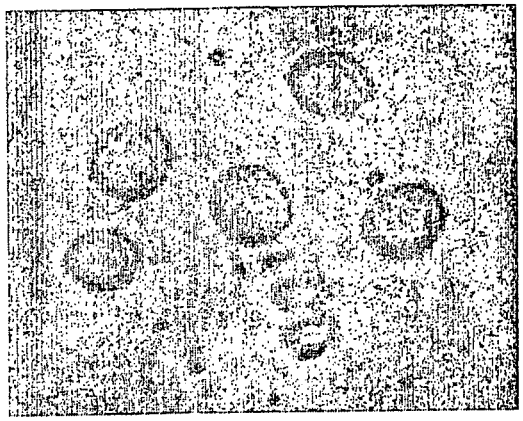
FIG. 2 represents a light micrograph of yeast cell walls encapsulating L-carvone.
Figure 3:
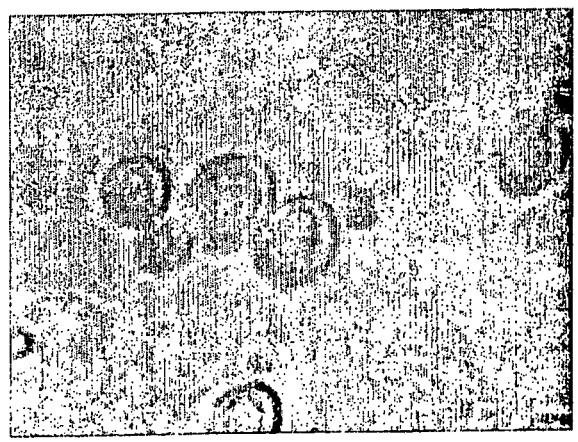
FIG. 3 represents a light micrograph of yeast cell walls encapsulating citral.
Figure 4:
FIG. 4 represents a light micrograph of terpene emulsion.
Figure 5:
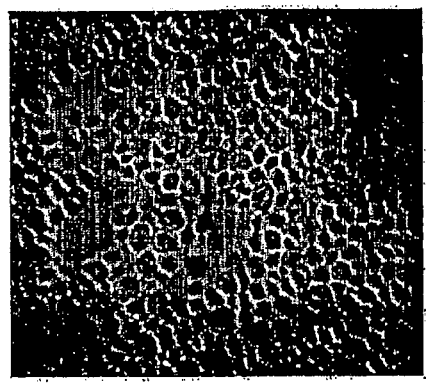
FIG. 5 represents a light micrograph of yeast cell walls in hydrodynamic volume (HV) water.
Figure 6:
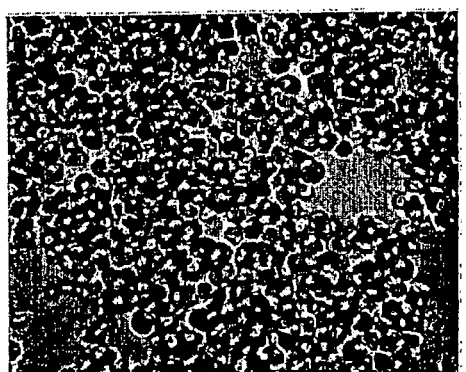
FIG. 6 represents a light micrograph of yeast cell walls encapsulating terpene in 5 times hydrodynamic volume (HV) of water.
Figure 7:
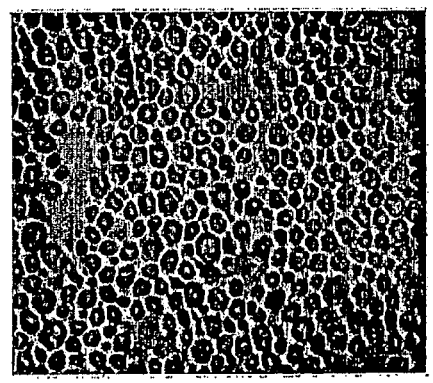
FIG. 7 represents a light micrograph of yeast cell walls encapsulating terpene in HV of water.
Figure 8:
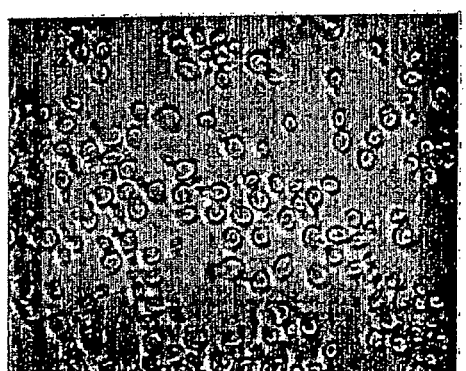
FIG. 8 represents a light micrograph of yeast cell walls encapsulating terpene in HV plus 5% of water.
Figure 9:
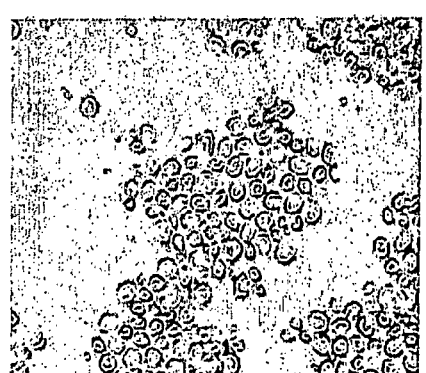
FIG. 9 represents a light micrograph of yeast cell walls encapsulating terpene in HV plus 10% of water.
Figure 10:
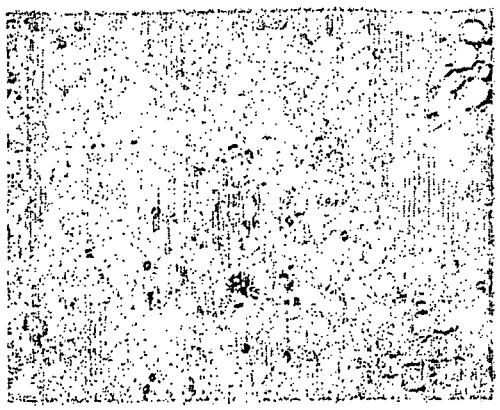
FIG. 10 represents a light micrograph of yeast cell walls encapsulating terpene in HV plus 20% of water.
Figure 11:
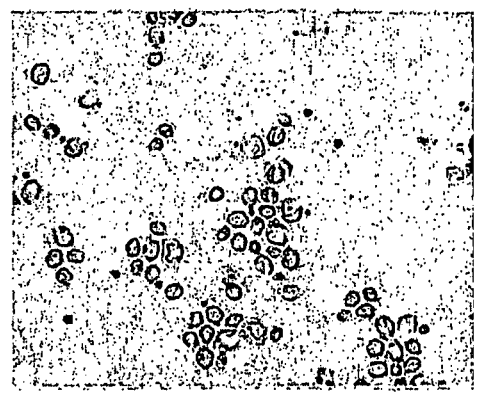
FIG. 11 represents a light micrograph of yeast cell walls encapsulating terpene in HV plus 30% of water.
Figure 12:
FIG. 12 represents a light micrograph of yeast cell walls encapsulating terpene in HV plus 40% of water.
Figure 13:
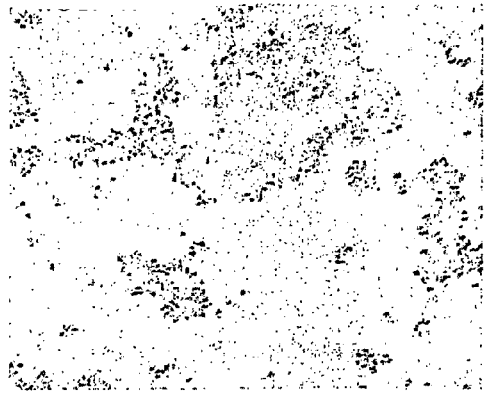
FIG. 13 represents a light micrograph showing the dispersal of dried hollow glucan particles encapsulating a terpene component and no xanthan gum.
Figure 14:
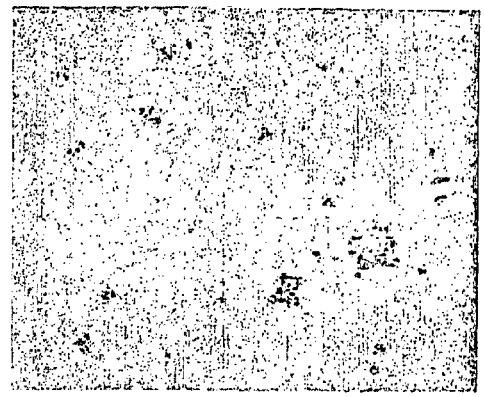
FIG. 14 represents a light micrograph as in FIG. 13 where 0.07 g of 1% xanthan gum is included.
Figure 15:
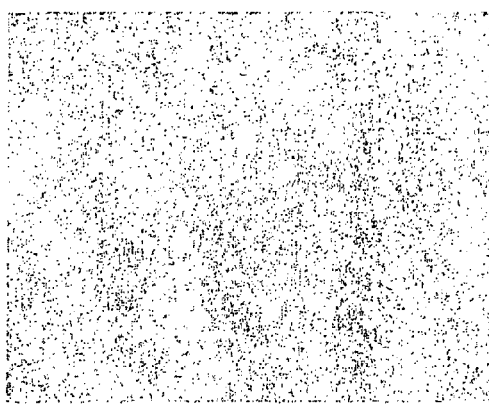
FIG. 15 represents a light micrograph as in FIG. 13 where 0.14 g of 1% xanthan gum is included.
Figure 16:
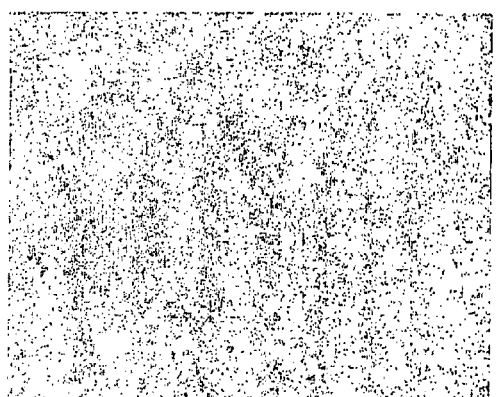
FIG. 16 represents a light micrograph as in FIG. 13 where 0.28 g of 1% xanthan gum is included.
Figure 17:
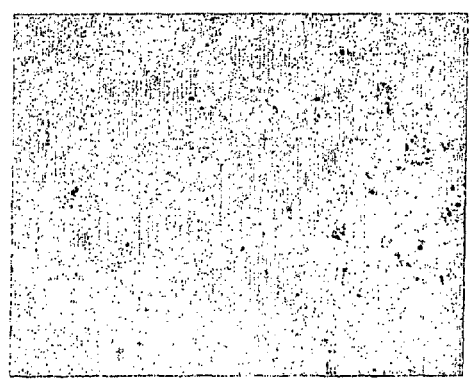
FIG. 17 represents a light micrograph as in FIG. 13 where 0.55 g of 1% xanthan gum is included.
Figure 18:
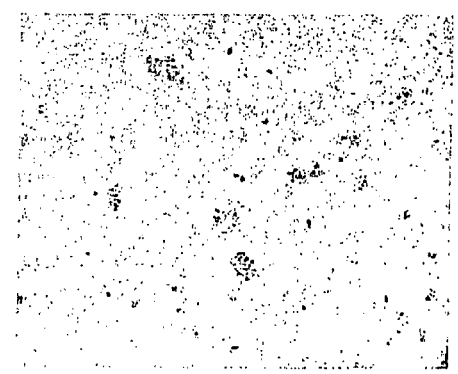
FIG. 18 represents a light micrograph as in FIG. 13 where 1.1 g of 1% xanthan gum is included.
Figure 19:
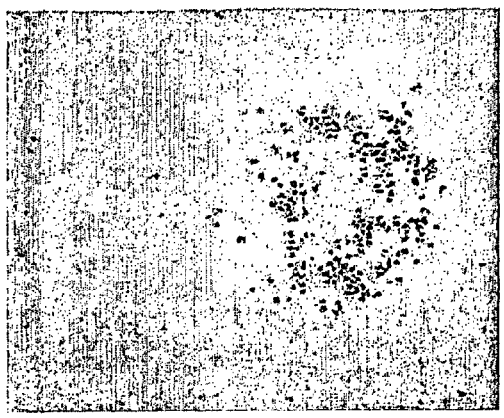
FIG. 19 represents a light micrograph as in FIG. 13 where 2.2 g of 1% xanthan gum is included.
Figure 20:
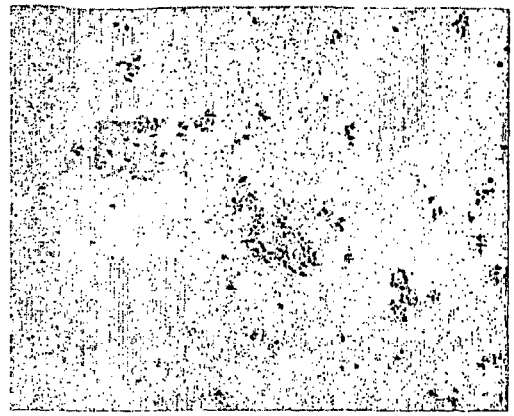
FIG. 20 represents a light micrograph as in FIG. 13 where 4.4 g of 1% xanthan gum is included.

FIG. 1 shows spherical structures with a dark area at their centre, these are empty hollow glucan particles. FIGS. 2 and 3 shows spherical structures with a swollen appearance with a light coloured interior, these are particles with terpene encapsulated in the central cavity—citral in FIG. 2 and L-carvone in FIG. 3. In FIGS. 2 and 3 small blobs of free terpene can also be seen, e.g. at the top of FIG. 2, just left of centre. FIG. 4 shows the terpene emulsion as small blebs of terpene suspended in water.

EXAMPLE 13

Determination of Maximal Citral and L-Carvone Loading Levels in Baker's Yeast Particles (YP)

The following protocol was performed to determine the maximal amounts of terpenes that would load into YP.

L-carvone and citral emulsions were prepared by sonicating 4.5 g of the terpene with 0.3 ml water.
10% Tween-80 solution was prepared by sonicating 4.5 g Tween-80 in 40.5 mls water.
YP suspension was prepared by mixing YP with water to form 20 mg/ml suspension.
Encapsulation reactions were set up as described in Table 21.

Citral or L-carvone-water emulsion was mixed with YP and Tween 80 surfactant overnight at room temperature. Samples were centrifuged at 14,000×g for 10 minutes and the appearance of free terpene floating on the aqueous layer was scored. The results are shown in the right hand column labelled free terpene of Table 21.

The expression "free terpene" refers to the visible presence of terpene in the centrifuged reaction mixture. The absence of free terpene indicates complete absorption of the terpene by the particles. The highest volume of terpene absorbed by the particles, as evidenced by the absence of free terpene, was recorded as the maximal volume of absorbed terpene emulsion.

TABLE 21

| Tube | 20 mg/ml YP μl | Terpene Emulsion | Vol μl | 10% Tween-80 μl | Free Terpene |
|---|---|---|---|---|---|
| 1 | 500 | — | — | 500 | − |
| 2 | 500 | L-carvone | 0.5 | 500 | − |
| 3 | 500 | L-carvone | 1.65 | 500 | − |
| 4 | 500 | L-carvone | 5 | 495 | − |
| 5 | 500 | L-carvone | 16.5 | 483.5 | − |
| 6 | 500 | L-carvone | 50 | 450 | + |
| 7 | 500 | L-carvone | 165 | 335 | + |
| 8 | 500 | L-carvone | 500 | — | + |
| 9 | 500 | Citral | 0.5 | 500 | − |
| 10 | 500 | Citral | 1.65 | 500 | − |
| 11 | 500 | Citral | 5 | 495 | − |
| 12 | 500 | Citral | 16.5 | 483.5 | +/− |
| 13 | 500 | Citral | 50 | 450 | + |
| 14 | 500 | Citral | 165 | 335 | + |
| 15 | 500 | Citral | 500 | — | + |

As can be seen from the results, YP is capable of absorbing and encapsulating at least 16.5 μl of L-carvone terpene emulsion or at least 5 μl of citral emulsion per 10 mg of YP.

EXAMPLE 14

Demonstration of Improved Terpene Loading with Surfactant and Determination of Optimal Tween-80:Terpene Ratio The following protocol was performed to demonstrate that the presence of surfactant improves terpene loading and to determine the minimum level of Tween-80 surfactant required for the YP terpene loading reaction.

L-carvone and citral emulsions were prepared by sonicating 4.5 g of the terpene with 0.3 ml water.
10% Tween-80 solution was prepared by sonicating 4.5 g Tween-80 in 40.5 ml water.
Baker's YP suspension was prepared by mixing YP with water to form 250 mg/ml suspension.
Loading reactions were set up as shown in Table 22 below.

Citral or L-carvone-water emulsion was mixed with YP with 0-10% v/v Tween 80 surfactant overnight at room temperature. Samples were centrifuged at 14,000×g for 10 minutes and the appearance of free terpene floating on the aqueous layer was scored. The results are shown in the right hand column labelled free terpene of Table 22.

The expression "free terpene" refers to the visible presence of terpene in the centrifuged reaction mixture. The absence of free terpene indicates complete absorption and encapsulation of the terpene by the YP. The highest volume of terpene absorbed by the YP, as evidenced by the absence of free terpene, was recorded as the maximal volume of absorbed terpene emulsion.

TABLE 22

| Tube | 250 mg/ml YP ml | Terpene Emulsion | Vol µl | 10% Tween-80 µl | Water µl | Free Terpene |
|---|---|---|---|---|---|---|
| 1 | 500 | — | — | — | 500 | − |
| 2 | 500 | L-carvone | 150 | 0 | 350 | Sl |
| 3 | 500 | L-carvone | 150 | 5 | 345 | Sl |
| 4 | 500 | L-carvone | 150 | 10 | 340 | Sl |
| 5 | 500 | L-carvone | 150 | 33 | 317 | Sl |
| 6 | 500 | L-carvone | 150 | 100 | 250 | − |
| 7 | 500 | L-carvone | 150 | 200 | 150 | − |
| 8 | 500 | L-carvone | 150 | 350 | — | − |
| 9 | 500 | L-carvone | 400 | 0 | 100 | ++ |
| 10 | 500 | L-carvone | 400 | 5 | 95 | ++ |
| 11 | 500 | L-carvone | 400 | 10 | 90 | ++ |
| 12 | 500 | L-carvone | 400 | 33 | 77 | ++ |
| 13 | 500 | L-carvone | 400 | 100 | — | + |
| 14 | 500 | L-carvone | 400 | 20 µl 100% | 30 | + |
| 15 | 500 | Citral | 113 | 0 | 387 | + |
| 16 | 500 | Citral | 113 | 5 | 382 | + |
| 17 | 500 | Citral | 113 | 10 | 377 | + |
| 18 | 500 | Citral | 113 | 33 | 354 | Sl |
| 19 | 500 | Citral | 113 | 100 | 287 | Sl |
| 20 | 500 | Citral | 113 | 200 | 187 | − |
| 21 | 500 | Citral | 113 | 350 | 37 | − |
| 22 | 500 | Citral | 250 | 0 | 250 | ++ |
| 23 | 500 | Citral | 250 | 5 | 245 | ++ |
| 24 | 500 | Citral | 250 | 10 | 240 | ++ |
| 25 | 500 | Citral | 250 | 33 | 217 | + |
| 26 | 500 | Citral | 250 | 100 | 150 | + |
| 27 | 500 | Citral | 250 | 20 µl 100% | 230 | + |

Sl = slight

As can be seen from the results a Tween-80 concentration of 1% (i.e. 100 µl of 10% Tween-80 in 1000 µl of reaction mixture) is sufficient to allow complete uptake of the terpene in the above reaction. A 2% Tween-80 causes no improvement in results, whereas with a 0.33% concentration free terpene was observed. This indicates that:
a) Terpenes are absorbed into YP particles in the absence of a surfactant, but the presence of surfactant significantly increases terpene absorption.
b) A Tween-80 concentration of around 1% is optimum for YP loading as it ensures proper loading whilst maximising the terpene payload of the YP particles.

EXAMPLE 15

Determination of Maximal Terpene Loading and Encapsulation at High Baker's Yeast Particles (YP) Levels The following protocol was performed to determine the maximal amounts of terpenes that would load into YP at high YP levels.
L-carvone and citral emulsions were prepared by sonicating 4.5 g of the terpene with 3 ml 1% Tween.
5% Tween-80 solution was prepared by sonicating 0.5 g Tween-80 in 9.5 ml water.
YP suspension was prepared by mixing YP with water to form 250 mg/ml suspension.

Encapsulation reactions were set up as shown in Table 23.

Citral or L-carvone-water emulsion was mixed with YP and Tween 80 surfactant overnight at room temperature. Samples were centrifuged at 14,000×g for 10 minutes and the appearance of free terpene floating on the aqueous layer was scored. The results are shown in the right hand column labelled free terpene of Table 23.

The expression "free terpene" refers to the visible presence of terpene in the centrifuged reaction mixture. The absence of free terpene indicates complete absorption of the terpene by the YP. The highest volume of terpene absorbed by the YP, as evidenced by the absence of free terpene, was recorded as the maximal volume of absorbed terpene emulsion.

TABLE 23

| Tube | 250 mg/ml YP µl | Terpene Emulsion | Vol µl | 1% Tween-80 µl | Free Terpene |
|---|---|---|---|---|---|
| 1 | 500 | — | — | 500 | − |
| 2 | 500 | L-carvone | 15 | 485 | − |
| 3 | 500 | L-carvone | 37.5 | 462.5 | − |
| 4 | 500 | L-carvone | 75 | 425 | − |
| 5 | 500 | L-carvone | 112.5 | 387.5 | − |
| 6 | 500 | L-carvone | 150 | 350 | Sl+ |
| 7 | 500 | L-carvone | 225 | 275 | + |
| 8 | 500 | L-carvone | 450 | 50 | + |
| 9 | 500 | Citral | 15 | 485 | − |
| 10 | 500 | Citral | 37.5 | 462.5 | − |
| 11 | 500 | Citral | 75 | 425 | − |
| 12 | 500 | Citral | 112.5 | 387.5 | Sl+ |
| 13 | 500 | Citral | 150 | 350 | + |
| 14 | 500 | Citral | 225 | 275 | + |
| 15 | 500 | Citral | 450 | 50 | + |

As can be seen from the results in Table 9, YP is capable of absorbing and encapsulating terpenes at high YP concentration. YP absorbed and encapsulated at least 112.5 µl of L-carvone terpene emulsion or at least 75 µl of citral emulsion per 125 mg of YP. This demonstrates that the terpene encapsulation reaction is independent of YP concentration within the ranges tested.

EXAMPLE 16

Screen Commercially Available Particles for Terpene Absorption

The following protocol was performed to analyse the loading properties of different types of particles. The particles studied were Baker's Yeast Particles (Sigma Chemical Corp., St. Louis, Mo.), Nutrex™ Walls (Sensient Technologies, Milwaukee, Wis.), SAF-Mannan™ (SAF Agri, Minneapolis, Minn.), Nutricept Walls™ (Nutricepts Inc., Burnsville, Minn.), Levacan™ (Savory Systems International, Inc., Branchburg, N.J.) and WGP™ (Alpha-beta Technology, Inc. Worcester, Mass.).

L-carvone and citral emulsions were prepared by sonicating 7 g terpene+3 ml 3.3% Tween-80.

Table 24 below compares the purity with the number of yeast particles per mg and the packed solids weight/volume ratio.

TABLE 24

| Yeast Particle | Purity % Beta 1,3-glucan | No. particles/mg | Mg particles/ml |
|---|---|---|---|
| Bakers | 11.2 | $4 \times 10^7$ | 250 |
| Nutrex | 24.5 | $1.7 \times 10^8$ | 58.8 |
| SAF Mannan | 33.4 | $2.4 \times 10^8$ | 41.7 |
|  |  | $2.7 \times 10^8$ |  |
| Nutricepts | 55.7 | $5.2 \times 10^8$ | 37 |
| Levacan | 74.6 | $1 \times 10^8$ | 19.2 |
| WGP | 82.1 | $3.5 \times 10^8$ | 10 |

From Table 24 it can be concluded that the number of particles per mg is inversely proportional to purity. Thus the number of particles per mg of WGP is almost 10-fold higher than Baker's YP.

The YP suspensions were prepared as follows:

Baker's yeast particle suspension (YP) was prepared by mixing 250 mg YP/ml 1% Tween 80.

Nutrex suspension was prepared by mixing 163 mg Nutrex YGP/ml 1% Tween 80.

SAF Mannan suspension was prepared by mixing 234 mg Biospringer YGP/ml 1% Tween 80.

Nutricepts suspension was prepared by mixing 99 mg Nutricepts YGP/ml 1% Tween 80.

Levacan suspension was prepared by mixing 217 mg Lev YGP/ml 1% Tween 80.

WGP suspension was prepared by mixing 121 mg WGP YGP/ml 1% Tween 80.

The packed volume of the above particles is identical which means that equal numbers of particles were assayed.

Loading reactions were set up as shown in Table 25 and left to incubate overnight. Samples were centrifuged at 14,000×g for 10 minutes and the appearance of free terpene floating on the aqueous layer and the color of the encapsulated terpenes in the pellet was scored. The results are shown in the two right hand columns of Table 25. The highest volume of terpene absorbed by particles as evidenced by the absence of free terpene was recorded as the volume of absorbed terpene emulsion.

From the results the following conclusions were reached:

Purified particles with a low lipid content were less effective at absorbing terpenes.

Less pure particles were more effective at absorbing terpenes.

Yellow degradation product of citral was not formed when encapsulated in SAF-Mannan™.

Based on qualitative loading at the single terpene level tested, SAF Mannan™ appears to be best, Nutrex™ second and Baker's third.

EXAMPLE 17

Kinetics of Terpene Loading into Various Types of Particles and Different Incubation Temperatures The following protocol was adopted to compare the loading kinetics of various types of yeast particles.

L-carvone and citral emulsions were prepared by sonicating 7 g terpene with 3 ml 3.3% Tween-80.

1% Tween-80 solution was prepared by sonicating 1 ml 10% Tween-80 in 10 ml water.

Baker's YP was prepared by mixing 5 g of bakers YP in 20 ml 1% Tween-80.

Nutrex™ YGP suspension was prepared by mixing 2 g Nutrexm YGP in 20 ml 1% Tween-80.

SAF Manna™ suspension was prepared by mixing 2 g SAF Mannan™ in 20 ml 1% Tween-80.

Loading reactions were set up as shown in Table 26.

The reactions were incubated for 1, 3, 6, 9 and 24 hours at room temperature or 37° C. After incubation samples were centrifuged at 14,000×g for 10 minutes and the appearance of free terpene floating on the aqueous layer was scored. The results are shown in the two right hand columns of Table 26. The highest volume of terpene absorbed by the particles as evidenced by the absence of free terpene was recorded as the volume of absorbed terpene emulsion. Colour of the encapsulated pellet was scored at 24 hours.

TABLE 25

| Tube | Particle | conc mg/ml | μl | Terpene Emulsion | Vol μl | 1% Tween 80 μl | Free Terpene | Colour |
|---|---|---|---|---|---|---|---|---|
| 1 | Baker's | 250 | 500 | L-carvone | 125 | 375 | − | W |
| 2 | Nutrex | 163 | 500 | L-carvone | 125 | 375 | − | W |
| 3 | SAF Mannan | 234 | 500 | L-carvone | 125 | 375 | − | W |
| 4 | Nutricepts | 99 | 500 | L-carvone | 125 | 375 | + | W |
| 5 | Levacan | 217 | 500 | L-carvone | 125 | 375 | + | W |
| 6 | WGP | 121 | 500 | L-carvone | 125 | 375 | + | W |
| 7 | Baker's | 250 | 500 | Citral | 100 | 375 | − | Y |
| 8 | Nutrex | 163 | 500 | Citral | 100 | 375 | − | Y |
| 9 | SAF Mannan | 234 | 500 | Citral | 100 | 375 | − | W |
| 10 | Nutricepts | 99 | 500 | Citral | 100 | 375 | + | Y |
| 11 | Levacan | 217 | 500 | Citral | 100 | 375 | + | int |
| 12 | WGP | 121 | 500 | Citral | 100 | 375 | + | int |
| 13 | — | — | — | L-carvone | 125 | 875 | + | — |
| 14 | — | — | — | Citral | 100 | 900 | + | Y |

W = white;
Y = yellow;
sl = sligh
int = intermediate

TABLE 26

| Tube | T °C. | Particle | conc mg/ml | µl | Terpene Emulsion | Vol µl | 1% Tween-80 | Free Terpene (hr) 1 | 3 | 6 | 9 | 24 | Color |
|---|---|---|---|---|---|---|---|---|---|---|---|---|---|
| 1 | Rt | Bakers | 250 | 3500 | L-carvone | 788 | 2712 | + | – | – | – | – | W |
| 2 | 37 | Bakers | 250 | 3500 | L-carvone | 788 | 2712 | + | – | – | – | – | W |
| 3 | Rt | Nutrex | 100 | 3500 | L-carvone | 1050 | 2450 | + | – | – | – | – | W |
| 4 | 37 | Nutrex | 100 | 3500 | L-carvone | 1050 | 2450 | + | – | – | – | – | W |
| 5 | Rt | SAF | 100 | 3500 | L-carvone | 1050 | 2450 | <+ | – | – | – | – | W |
| 6 | 37 | SAF | 100 | 3500 | L-carvone | 1050 | 2450 | <+ | – | – | – | – | W |
| 7 | Rt | Bakers | 250 | 3500 | Citral | 525 | 2975 | + | – | – | – | – | Y |
| 8 | 37 | Bakers | 250 | 3500 | Citral | 525 | 2975 | + | – | – | – | – | VY |
| 9 | Rt | Nutrex | 100 | 3500 | Citral | 788 | 2712 | + | – | – | – | – | Y |
| 10 | 37 | Nutrex | 100 | 3500 | Citral | 788 | 2712 | + | – | – | – | – | VY |
| 11 | Rt | SAF | 100 | 3500 | Citral | 788 | 2712 | + | – | – | – | – | W |
| 12 | 37 | SAF | 100 | 3500 | Citral | 788 | 2712 | + | – | – | – | – | W |

White, W;
Yellow, Y;
Very Yellow, VY;
Room Temperature, Rt

From the results shown in Table 26 and other observations the following conclusions can be made:
Terpene loading reaction takes between 1 and 3 hours.
Terpene loading occurs faster at 37° C. than at room temperature.
SAF Mannan™ appears to be preferable particles for two reasons:
  Faster and more complete uptake of both terpenes.
  Citral remains stable when loaded as evidenced by the absence of yellow colour, characteristic of citral degradation, after 24 hours at 37° C.

EXAMPLE 18

Screen a Range of Single Terpenes and Terpene Combinations for Particle Loading The following protocol was adopted to compare the loading efficiency of Baker's YP versus SAF Mannan™.
Terpene emulsions were prepared as follows:
L-carvone—4.5 g L-carvone in 1.5 ml 3.3% Tween-80.
Citral—4.5 g citral in 1.5 ml 3.3% Tween-80.
Thymol/L-carvone mixture (T/L)-2.25 g thymol and 2.25 g L-carvone in 1.5 ml 3.3% Tween-80.
Eugenol—4.5 g eugenol in 1.5 ml 3.3% Tween-80.
Geraniol—4.5 g geraniol in 1.5 ml 3.3% Tween-80.
Citral/L-carvone/Eugenol mixture (C/L/E)—1.5 g citral, 1.5 g L-carvone, 1.5 g eugenol in in 1.5 ml 3.3% Tween-80.
Emulsions composed of terpene:water:surfactant ratio of 0.75:0.3:0.05 were used for these experiments.
Increasing volumes of terpene emulsion were mixed with 250 mg/ml Baker's YP or 250 mg/ml SAF Mannan™ overnight at room temperature as shown in Tables 27 and 28. Samples were centrifuged at 14,000×g for 10 minutes and the appearance of free terpene floating on the aqueous layer was scored. The highest volume of terpene emulsion absorbed by Baker's YP or SAF Mannan™ as evidenced by the absence of free terpene was recorded as the volume of absorbed terpene emulsion. Colour of encapsulated terpenes in the pellet was recorded. The results in Tables 27 and 28 show that all single and terpene combinations were efficiently loaded into both Baker's YP or SAF Mannan particles.

TABLE 27

Evaluation of Baker's YP Loading of Different Terpenes and Terpene Mixtures.

| Tube | Baker (µl) | Terpene Emulsion | Vol (µl) | 1% Tween-80 (µl) | Free Terpene | Colour |
|---|---|---|---|---|---|---|
| 1 | 500 | — | — | 500 | – | W |
| 2 | 500 | L-carvone | 15 | 485 | – | W |
| 3 | 500 | L-carvone | 37.5 | 462.5 | – | W |
| 4 | 500 | L-carvone | 7 | 425 | +/– | W |
| 5 | 500 | L-carvone | 112.5 | 387.5 | +/– | W |
| 6 | 500 | L-carvone | 150 | 350 | + | W |
| 7 | 500 | L-carvone | 225 | 275 | + | W |
| 8 | 500 | L-carvone | 450 | 50 | ++ | W |
| 9 | 500 | Citral | 15 | 485 | – | Y |
| 10 | 500 | Citral | 37.5 | 462.5 | – | Y |
| 11 | 500 | Citral | 75 | 425 | – | Y |
| 12 | 500 | Citral | 112.5 | 387.5 | +/– | Y |
| 13 | 500 | Citral | 150 | 350 | + | Y |
| 14 | 500 | Citral | 225 | 275 | + | Y |
| 15 | 500 | Citral | 450 | 50 | + | Y |
| 16 | 500 | T/L | 15 | 485 | – | W |
| 17 | 500 | T/L | 37.5 | 462.5 | – | W |
| 18 | 500 | T/L | 75 | 425 | – | W |
| 19 | 500 | T/L | 112.5 | 387.5 | +/– | W |
| 20 | 500 | T/L | 150 | 350 | + | W |
| 21 | 500 | T/L | 225 | 275 | + | W |
| 22 | 500 | T/L | 450 | 50 | + | W |
| 23 | 500 | Eugenol | 15 | 485 | – | W |
| 24 | 500 | Eugenol | 37.5 | 462.5 | – | W |
| 25 | 500 | Eugenol | 75 | 425 | – | W |
| 26 | 500 | Eugenol | 112.5 | 387.5 | +/– | W |
| 27 | 500 | Eugenol | 150 | 350 | + | W |
| 28 | 500 | Eugenol | 225 | 275 | + | W |
| 29 | 500 | Eugenol | 450 | 50 | + | W |
| 30 | 500 | Geraniol | 15 | 485 | – | W |
| 31 | 500 | Geraniol | 37.5 | 462.5 | – | W |
| 32 | 500 | Geraniol | 75 | 425 | – | W |
| 33 | 500 | Geraniol | 112.5 | 387.5 | + | W |
| 34 | 500 | Geraniol | 150 | 350 | + | W |
| 35 | 500 | Geraniol | 225 | 275 | + | W |
| 36 | 500 | Geraniol | 450 | 50 | + | W |
| 37 | 500 | C/L/E | 15 | 485 | – | Y |
| 38 | 500 | C/L/E | 37.5 | 462.5 | – | Y |
| 39 | 500 | C/L/E | 75 | 425 | – | Y |
| 40 | 500 | C/L/E | 112.5 | 387.5 | +/– | Y |
| 41 | 500 | C/L/E | 150 | 350 | + | Y |
| 42 | 500 | C/L/E | 225 | 275 | + | Y |
| 43 | 500 | C/L/E | 450 | 50 | + | Y |

TABLE 28

Evaluation of SAF Mannan Loading of Different Terpenes and Terpene Mixtures.

| Tube | SAF (µl) | Terpene Emulsion | Vol | 1% Tween-80 (µl) | Free Terpene | Colour |
|---|---|---|---|---|---|---|
| 1 | 500 | — | — | 500 | − | W |
| 2 | 500 | L-carvone | 15 | 485 | − | W |
| 3 | 500 | L-carvone | 37.5 | 462.5 | − | W |
| 4 | 500 | L-carvone | 75 | 425 | − | W |
| 5 | 500 | L-carvone | 112.5 | 387.5 | − | W |
| 6 | 500 | L-carvone | 150 | 350 | +/− | W |
| 7 | 500 | L-carvone | 225 | 275 | +/− | W |
| 8 | 500 | L-carvone | 450 | 50 | + | W |
| 9 | 500 | Citral | 15 | 485 | − | W |
| 10 | 500 | Citral | 37.5 | 462.5 | − | W |
| 11 | 500 | Citral | 75 ul | 425 | − | W |
| 12 | 500 | Citral | 112.5 | 387.5 | − | W |
| 13 | 500 | Citral | 150 | 350 | +/− Inverted | W |
| 14 | 500 | Citral | 225 | 275 | + Inverted | W |
| 15 | 500 | Citral | 450 | 50 | + Inverted | W |
| 16 | 500 | T/L | 15 | 485 | − | W |
| 17 | 500 | T/L | 37.5 | 462.5 | − | W |
| 18 | 500 | T/L | 75 | 425 | − | W |
| 19 | 500 | T/L | 112.5 | 387.5 | − | W |
| 20 | 500 | T/L | 150 | 350 | +/− | W |
| 21 | 500 | T/L | 225 | 275 | + | W |
| 22 | 500 | T/L | 450 | 50 | + | W |
| 23 | 500 | Eugenol | 15 | 485 | − | W |
| 24 | 500 | Eugenol | 37.5 | 462.5 | − | W |
| 25 | 500 | Eugenol | 75 | 425 | − | W |
| 26 | 500 | Eugenol | 112.5 | 387.5 | +/− | W |
| 27 | 500 | Eugenol | 150 | 350 | + | W |
| 28 | 500 | Eugenol | 225 | 275 | + | W |
| 29 | 500 | Eugenol | 450 | 50 | + | W |
| 30 | 500 | Geraniol | 15 | 485 | − | W |
| 31 | 500 | Geraniol | 37.5 | 462.5 | − | W |
| 32 | 500 | Geraniol | 75 | 425 | − | W |
| 33 | 500 | Geraniol | 112.5 | 387.5 | − | W |
| 34 | 500 | Geraniol | 150 | 350 | − | W |
| 35 | 500 | Geraniol | 225 | 275 | − Inverted | W |
| 36 | 500 | Geraniol | 450 | 50 | + Inverted | W |
| 37 | 500 | C/L/E | 15 | 485 | − | W |
| 38 | 500 | C/L/E | 37.5 | 462.5 | − | W |
| 39 | 500 | C/L/E | 75 | 425 | − | W |
| 40 | 500 | C/L/E | 112.5 | 387.5 | − | W |
| 41 | 500 | C/L/E | 150 | 350 | − | W |
| 42 | 500 | C/L/E | 225 | 275 | +/− | W |
| 43 | 500 | C/L/E | 450 | 50 | + | W |

Inverted = Phase Inverted – solids floating on top
− no free oil;
W = white;
Y = yellow.

From the results the following observations were made:
All terpenes appeared to load into Baker's YP and SAF Mannan.
SAF Mannan has a higher terpene loading capacity than bakers YP.
The two and three way mixtures of terpenes also appear to efficiently load.
The terpene Eugenol appears to have a higher density than the particles and water as it was found associated with the pellet.
For the SAF Mannan, the higher load levels and lighter particles resulted in loaded particles floating on the surface of the aqueous layer for citral and geraniol.
Citral was protected from oxidation by the SAF Mannan but not by the Baker's YP.
The approximate maximal loading for each particle type was determined and is shown in tables 29 and 30 below.

Percentage loaded represents a ratio of the amount of terpene loaded to the amount of particle present (weight for weight).

TABLE 29

Maximal terpene loading in Baker's YP.

| Terpene | Vol. Loaded µl | % Loaded w/w |
|---|---|---|
| L-carvone | 37.5 | 33.3 |
| Citral | 75 | 67% |
| Thymol/L-carvone 1:1 | 75 | 67% |
| Eugenol | 75 | 67% |
| Geraniol | 75 | 67% |
| Citral/L-carvone/Eugenol (1:1:1) | 75 | 67% |

TABLE 30

Maximal terpene loading in SAF Mannan.

| Terpene | Vol. loaded µl | % Loaded w/w |
|---|---|---|
| L-carvone | 112.5 | 100% |
| Citral | 150 | 133% |
| Thymol/L-carvone 1:1 | 112.5 | 100% |
| Eugenol | 112.5 | 100% |
| Geraniol | 150 | 133% |
| Citral/L-carvone/Eugenol (1:1:1) | 150 | 133% |

EXAMPLE 19

Evaluation of Terpene Stability in Aqueous Emulsions and Encapsulated Terpene Formulations Terpene stability was assessed by the observation of citral formulations for the formation of a yellow colored oxidation product. As noted in the right hand column in Tables 25-28 citral emulsions and citral encapsulated Bakers YP turned a progressively increasing yellow color over time. However, citral encapsulation in SAF Mannan™ increased citral stability as evidenced by a reduction or absence of yellow color over time.

EXAMPLE 20

Loading of Terpenes in Minimal Water

The following protocol was carried out to evaluate the possibility that terpene loading and encapsulation into YP could be carried out at a very high Yeast Particles (YP) solids level to allow for direct extrusion of the loaded formulation into a fluidised bed drier. The minimal amount of water to completely hydrate the SAF Mannan™ particles was determined to be 3.53 g water per g solids. This defines the hydrodynamic volume (HV) or water absorptive capacity of the particles. At this level of water the hydrated particles have a consistency of a stiff dough which is thixotropic, i.e. shear thinning like mayonnaise. Addition of water up to 40% above the HV results in a thick flowable paste. The standard reaction that has been used in the above examples was carried out at 3×HV water.

A series of terpene (L-carvone) loading reactions were carried out keeping the ratio of particle:terpene:Tween (1:0.44:0.04) constant and varying the amount of water in the system from the HV (3.53 g) to HV+40% water (4.92 g). Controls were the standard loading system which uses 3×HV water, particles only and terpene only reactions. Following overnight incubation samples of the mixtures were evaluated microscopically for free terpene and evidence of terpene uptake into the particles and for material flow characteristics by assessing flow in inverted tubes over 15 minutes. In addition, the presence of free oil was assessed by hydrating the reaction mixture with 5×HV, vortexing to obtain a complete dispersion of particles and centrifugation to sediment the particle encapsulated terpene. The results are shown in Table 31 and FIGS. 7 to 12. FIGS. 7 to 12 show the loading results of the following tubes:

FIG. 7—Tube 3

FIG. 8—Tube 5

FIG. 9—Tube 6

FIG. 10—Tube 8

FIG. 11—Tube 10

FIG. 12—Tube 11

TABLE 31

| Tube | SAF g | Terpene Emulsion | Weight (g) | Water (g) | Free Terpene | Flow |
|---|---|---|---|---|---|---|
| 1 | — | L-carvone | 4.64 | 4.5 | + | + |
| 2 | 1 | — | — | 8.0 | − | + |
| 3 | 1 | L-carvone | 4.64 | 4.5 | − | + |
| 4 | 1 | L-carvone | 4.64 | — | − | − |
| 5 | 1 | L-carvone | 4.64 | 0.17 | − | − |
| 6 | 1 | L-carvone | 4.64 | 0.35 | − | − |
| 7 | 1 | L-carvone | 4.64 | 0.52 | − | Sl |
| 8 | 1 | L-carvone | 4.64 | 0.7 | − | Mod |
| 9 | 1 | L-carvone | 4.64 | 0.87 | − | High |
| 10 | 1 | L-carvone | 4.64 | 1.05 | − | High |
| 11 | 1 | L-carvone | 4.64 | 1.39 | − | High |

The results shown in Table 31 and FIGS. 7 to 12 demonstrate that terpene loading and encapsulation into the particles occurred at all water ratios evaluated. Surprisingly, equivalent loading occurred even when the loading reaction was taking place in a reaction with the consistency of a stiff dough using the minimal amount of water to hydrate the particles. The absence of free terpene was observed microscopically (FIGS. 7 to 12) and in the low level of terpene in the supernatants, as evidenced by a marked reduction in the turbidity of the supernatant compared to the terpene only control.

These results extend our understanding of the conditions to load terpenes into hollow glucan particles. The flexibility to use a minimal volume of water to hydrate the particles during the loading process will allow loading of the terpenes under conditions where the reaction mixture is a malleable dough-like consistency using standard food-grade swept surface dough mixers. The consistency of the final high solids terpene loaded mixture is suitable for direct extrusion to form noodles and pellets for fluidised bed drying.

Suitable facilities to scale up production in this manner would require:

Gaulin homogeniser, or equivalent to produce stable terpene emulsion.

Swept surface dough mixing tank.

Extruder.

Fluidised bed drier.

EXAMPLE 21

Evaluation of an Interstitial Hydrocolloid Agent to Aid Dispersion in Dried Hollow Glucan Particles Encapsulating a Terpene Component Dispersion when Re-Hydrated The following protocol was adopted to evaluate the effect of an interstitial hydrocolloid to increase dried hollow glucan particle encapsulated terpene formulations to disperse when hydrated.

SAF Mannan™ particles 0.1% Tween 80

L-carvone

Xanthan Gum—1% w/v in 0.1% Tween 80

The effect of increasing xanthan gum levels on dry hollow glucan particle encapsulated L-carvone dispersion in water was assessed by loading L-carvone into SAF Mannan by incubating 1.1 g of an L-carvone emulsion (L-carvone:water:surfactant ratio of 0.75:0.3:0.05) with 1 g SAF Mannan and 4.4 g 0.1% Tween 80 containing 0-1% xanthan gum as shown in Table 32.

TABLE 32

| Tube | SAF g | L-carvone Emulsion (g) | 0.1% Tween-80 (g) | 1% Xanthan (g) | Visual Observations |
|---|---|---|---|---|---|
| 1 | 1 | 1.1 | 4.4 | 0 | Large non-uniform clumps |
| 2 | 1 | 1.1 | 4.33 | 0.07 | Uniform suspension |
| 3 | 1 | 1.1 | 4.26 | 0.14 | Uniform suspension |
| 4 | 1 | 1.1 | 4.12 | 0.28 | Uniform suspension |
| 5 | 1 | 1.1 | 3.85 | 0.55 | Uniform suspension |
| 6 | 1 | 1.1 | 3.3 | 1.1 | Finer Uniform suspension |
| 7 | 1 | 1.1 | 2.2 | 2.2 | Finer Uniform suspension |
| 8 | 1 | 1.1 | 0 | 4.4 | Finer Uniform suspension |

The results in Table 32 and FIGS. 13 to 20 demonstrate that the inclusion of a high molecular weight hydrocolloid during the drying of the particle encapsulated terpene aids in the hydration and dispersion of the microparticles into a uniform suspension. Other examples of such hydrocolloid agents are maltodextrin, alginates, or the like.

It may also be worthwhile to include a pellet coating to increase the stability of the loaded terpenes, and to provide a sustained release of terpene.

EXAMPLE 22

Nematocidal Activity of Encapsulated Terpenes

Preparations of yeast cell walls encapsulating citral were prepared according to the procedures described above. The hollow glucan particles contained 17.5% citral, and the particles were present at in the test preparations at a concentration of 1000 ppm. This means that terpenes were effectively present at a concentration of 175 ppm.

1.0 ml of the test preparations was added to 0.1 to 0.15 ml of water containing root-knot nematodes. 1.0 water was added to the nematodes as the control.

Observations were made as [revopis; u described and the kill rate assessed (i.e. percentage dead) after 24 and 48 hrs. The results shown below in Table 13 are an average of 2 sets of results.

TABLE 33

Nematicidal activity of encapsulated terpene solution (17.5% citral @ 1000 ppm)

| Time | Kill Rate | |
|---|---|---|
| | Test | Control |
| 24 h | 45 | 17 |
| 48 h | 56 | 21 |

The results demonstrate that hollow glucan particles encapsulating terpenes are effective at killing root-knot nematodes at a particle concentration of 1000 ppm, which corresponds to a citral concentration of only 175 ppm.

Thus hollow glucan particles encapsulating terpenes appear to be as effective as terpenes in solution or with surfactant as nematicides. The nematicidal activity is retained despite the terpene being encapsulated within the particle. It can be expected that higher concentrations of terpenes within the hollow glucan particles, or higher concentrations of the particles would result in an even higher kill rate, as is the case for terpenes in solution or with surfactant.

The invention claimed is:

1. A method of killing plant parasitic nematodes, said method comprising applying an effective amount of a nematicidal composition comprising hollow glucan particles, wherein the hollow glucan particles encapsulate a terpene component comprising a combination of thymol and geraniol, wherein the hollow glucan particles have a lipid content greater than 5% w/w, and wherein the nematicidal composition kills plant parasitic nematodes and wherein the composition comprises a surfactant which holds the terpene component in solution.

2. The method according to claim 1 wherein the nematicidal composition further comprises an excipient.

3. The method according to claim 1 wherein the hollow glucan particles are yeast cell walls or hollow whole glucan particles.

4. The method according to claim 3 wherein the yeast cell walls are derived from Baker's yeast cells.

5. The method according to claim 3 wherein the hollow glucan particles are obtained from the insoluble waste stream of a yeast extract manufacturing process.

6. The method according to claim 3 wherein the glucan particles are alkali extracted.

7. The method according to claim 3 wherein the glucan particles are acid extracted.

8. The method according to claim 1 wherein the hollow glucan particles have a lipid content greater than 10% w/w.

9. The method according to claim 1 wherein the surfactant is selected from the group consisting of sodium lauryl sulphate, polysorbate 20, polysorbate 80, polysorbate 40, polysorbate 60, polyglyceryl ester, polyglyceryl monooleate, decaglyceryl monocaprylate, propylene glycol dicaprilate, triglycerol monostearate, polyoxyethylenesorbitan monooleate, sorbitan monolaurate, sorbitan monopalmitate, sorbitan monostearate, sorbitan monooleate, polyoxyethylene (4) lauryl ether and mixtures thereof.

10. A method of preparing a composition for killing plant parasitic nematodes, the composition comprising hollow glucan particles encapsulating a terpene component and wherein the terpene component comprises a combination of thymol and geraniol, said method comprising;
   a) providing the terpene component and a surfactant which holds the terpene component in solution in water;
   b) providing hollow glucan particles;
   c) incubating the terpene component with the glucan particles under suitable conditions for terpene encapsulation; and
   d) recovering the glucan particles encapsulating the terpene component.

11. The method according to claim 10 further comprising the step of drying the glucan particles encapsulating the terpene component.

12. The method according to claim 11 wherein the drying is achieved by freeze drying, fluidized bed drying, drum drying or spray drying.

13. The method according to claim 10 wherein in step a) the terpene component is provided as a suspension in an aqueous solvent.

14. The method according to claim 10 wherein the solvent is water.

15. The method according to claim 10 wherein the surfactant is present at a concentration of 0.1 to 10% by volume of the nematicidal composition.

16. The method according to claim 10 wherein the terpene component is provided as a true solution in water.

17. The method according to claim 10 wherein in step b), the hollow glucan particles are provided as a suspension in a solvent.

18. The method according to claim 17 wherein the suspension comprises 1 to 1000 mg glucan particles per ml.

19. The method according to claim 18 wherein the suspension comprises 200 to 400 mg glucan particles per ml.

20. The method according to claim 10 wherein the hollow glucan particles are provided as a dry powder and added to the terpene-surfactant suspension.

21. The method according to claim 10 wherein the glucan particles are provided in between the hydrodynamic volume and 1.5 times the hydrodynamic volume of water.

22. The method according to claim 11 wherein the conditions of step c) are atmospheric pressure and a temperature of 20 to 37° C.

23. A method of killing plant parasitic nematodes, said method comprising applying an effective amount of a nematicidal composition comprising hollow glucan particles, wherein the hollow glucan particles encapsulate a terpene component and wherein the terpene component comprises a combination of thymol and geraniol, wherein the hollow glucan particles have a lipid content greater than 5% w/w, and wherein the nematicidal composition kills plant parasitic nematodes.

24. A method of killing plant parasitic nematodes, said method comprising: applying an effective amount of a nematicidal composition comprising hollow glucan particles, wherein the hollow glucan particles encapsulate a terpene component comprising a combination of thymol and geraniol, wherein the hollow glucan particles have a lipid content greater than 5% w/w, and wherein the nematicidal composition kills plant parasitic nematodes.

* * * * *